(12) United States Patent
Wu

(10) Patent No.: US 7,399,754 B2
(45) Date of Patent: Jul. 15, 2008

(54) N²-QUINOLINE OR ISOQUINOLINE SUBSTITUTED PURINE DERIVATIVES

(76) Inventor: Zhanggui Wu, 197 Kent St., Apartment 31, Brookline, MA (US) 02446

( * ) Notice: Subject to any disclaimer, the term of this patent is extended or adjusted under 35 U.S.C. 154(b) by 217 days.

(21) Appl. No.: 11/452,955

(22) Filed: Jun. 15, 2006

(65) Prior Publication Data

US 2006/0293274 A1 Dec. 28, 2006

Related U.S. Application Data

(63) Continuation of application No. PCT/CN2006/000113, filed on Jan. 23, 2006.

(30) Foreign Application Priority Data

Jun. 16, 2005 (CN) .......................... 2005 1 0026846

(51) Int. Cl.
*A01N 43/04* (2006.01)
*A61K 31/70* (2006.01)
*C07H 19/00* (2006.01)
*C07H 19/22* (2006.01)

(52) U.S. Cl. .......................... 514/48; 514/43; 514/45; 514/46; 514/47; 536/27.1; 536/27.13

(58) Field of Classification Search ........................ None
See application file for complete search history.

(56) References Cited

U.S. PATENT DOCUMENTS 5,604,210 A * 2/1997 Nagaoka et al. ................ 514/46
6,589,950 B1 * 7/2003 Collingwood et al. ..... 514/234.2

* cited by examiner

*Primary Examiner*—Patrick T Lewis
(74) *Attorney, Agent, or Firm*—Kening Li

(57) ABSTRACT

Novel compound having the following formula:

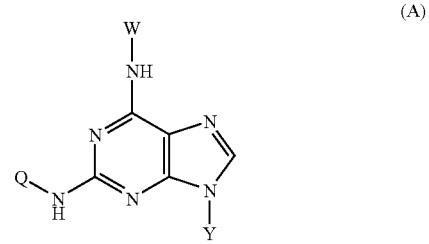

(A)

wherein W represents a hydrogen, an optionally substituted $C_{1-6}$ alkyl, an optionally substituted $C_{3-6}$ cycloalkyl, or an optionally substituted $C_{1-6}$ haloalkyl, Y represents a hydrogen, or a saccharide, Q represents a quinoline or isoquinoline. Also disclosed are a pharmaceutical compositions comprising the same, methods for treating cancer using the same, and methods for the synthesis of the same.

24 Claims, No Drawings

N²-QUINOLINE OR ISOQUINOLINE SUBSTITUTED PURINE DERIVATIVES

CROSS REFERENCE TO RELATED APPLICATIONS

The present application claims priority to Chinese Patent application No. 2005-10026846.3, filed Jun. 16, 2005, and International Patent Application No. PCT/CN2006/000113, filed Jan. 23, 2006, designating the United States of America, the entire disclosure of which is incorporated herein by reference.

FIELD OF INVENTION

The present invention relates to N²-quinoline or isoquinoline substituted purine derivatives, processes for their production, pharmaceutical compositions comprising the same, and methods for using the compounds in the treatment of cancer.

BACKGROUND OF THE INVENTION

Cancer remains a major threat to human health, and millions of people die from cancers every year in the world. Although many methods of treatment, such as surgery and radiation therapy are available, curative ratio generally is low. Presently, the use of pharmaceutical chemicals remains one of the most effective cancer therapies.

Purine or pyridine derivatives are known to have anti-viral or anti-cancer activities, see e.g. EP 173624, EP 253412, EP 353955, WO 9201698, and EP 481214.

In natural or synthetic nucleotide derivatives, the pyridine or purine or other heterocylic group is located on the 1 position of the saccharide ring (corresponding to the 2 position of a hydroxyl-substituted furan derivative). These substitutes have recently been reported to have anti-cancer or antivirus activities.

Another group of derivatives, O⁶-alkyl purine derivatives, are known to have the ability to inhibit the activity of O⁶-alkylguanine-DNA alkyltransferase (AGT), thereby enhancing the effectiveness of alkylating agent as tumor chemotherapy agents. Although the cancer cell killing mechanism of the O⁶-methyl guanine is not clear, it is generally understood that the mechanism of the O⁶-chloroethyl guanine is via a cycloethidene guanine intermediate, which cross links the DNA double strand. This linkage can be eliminated or prevented via an ATPase mediated de-chloroethylation, e.g. via AGT. Methods for antagonizing AGT have been reported in e.g. U.S. Pat. No. 5,091,430 and WO 9113898.

N-substituted purine derivatives have been known. For example, N⁶-disubstituted purine derivatives are described in U.S. Pat. No. 4,853,386, which can be used to treat allergies. 6-cyclopropylamino-9H purine derivatives are described in JP 2003-55377 and JP 2003-119197, which have antivirus activities. Glycosylated purine derivatives which have anti-inflammatory properties are described in J. Org. Chem (2004, 69:3212-3215). N²-butylphenyl-2'-desoxypurine derivatives are described in J. Med. Chem (1984, 27:175-181), which have the activity of inhibiting eukaryotic DNAα polymerase. 2, 6, 9-substituted purine derivatives are described in the Tetrahedron Letters (1998, 39:1827-1830).

None of the above mentioned compounds, however, have been shown to have anti-cancer activities or the ability to inhibit abnormal cell growth. Accordingly, there is a need for N²-substituted purine derivatives that may be used as anti-cancer agents.

DESCRIPTION OF THE INVENTION

The present invention relates to highly stable N²-substituted purine derivatives with low toxicity and high anti-cancer activities.

The present invention relates to compounds having the following formula:

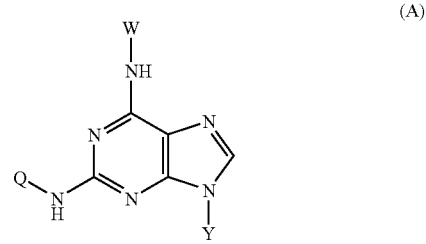

(A)

wherein,

W represents a hydrogen, an optionally substituted $C_{1-6}$ alkyl, an optionally substituted $C_{3-6}$ cycloalkyl, or an optionally substituted $C_{1-6}$ haloalkyl, Y represents hydrogen, or a saccharide, wherein the saccharide is preferably one of the following:

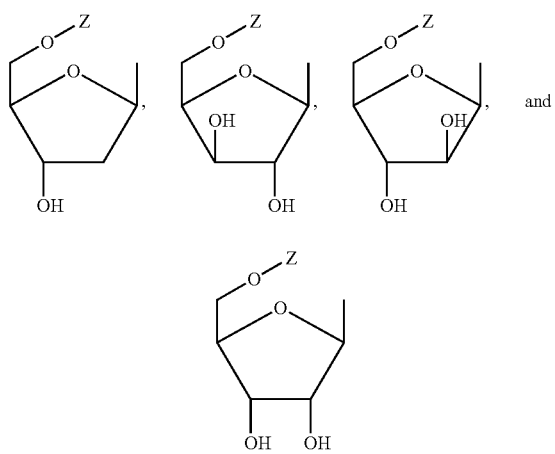

Wherein
Z represents hydrogen, or one of the following:

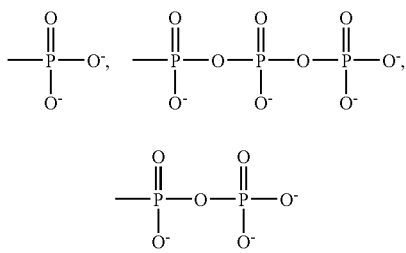

Q represents one of the following:

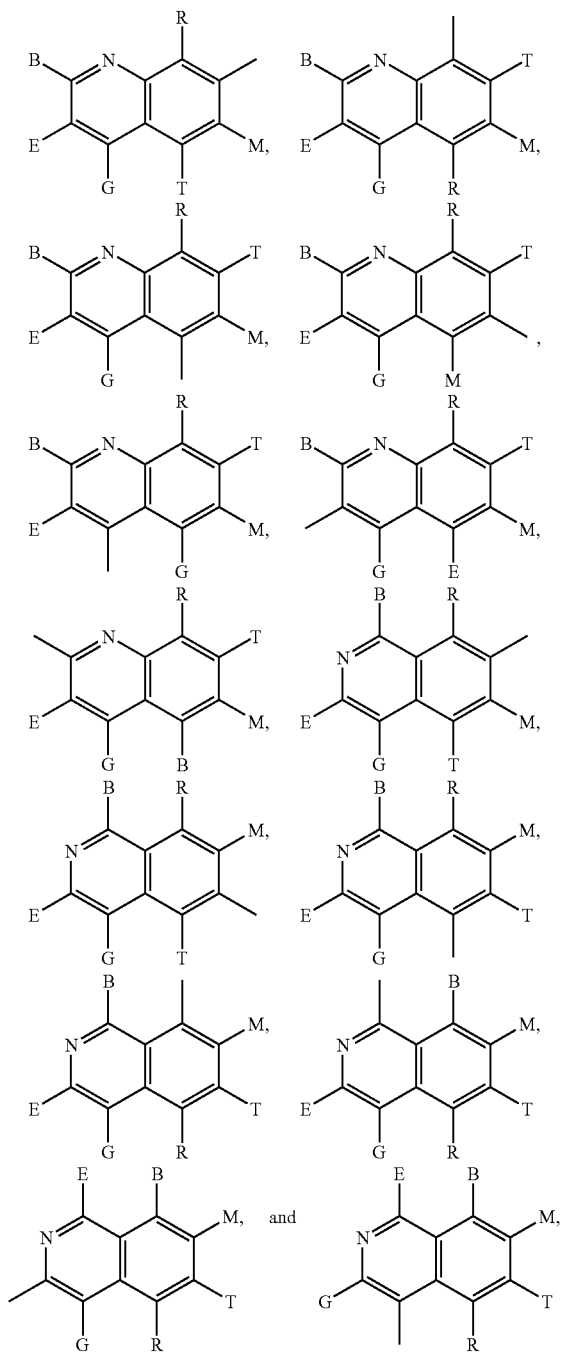

wherein each of B, E, G, R, T, or M independently represents a hydrogen, an $C_{1-6}$ alkyl, an $C_{3-6}$ haloalkyl, a halogen, a cyano, or an amino group, optionally in the form of their racemates, their pure stereoisomers, in particular enantiomers or diastereomers, or in the form of mixtures of stereoisomers, in particular the enantiomers or diastereomers, in any mixing ratio; in the illustrated form or in the form of their acids or their bases or in the form of their salts, in particular physiologically acceptable salts, or in the form of their solvates, in particular the hydrates.

Preferably, in the compound of the present invention having formula A, W represents one of the following:

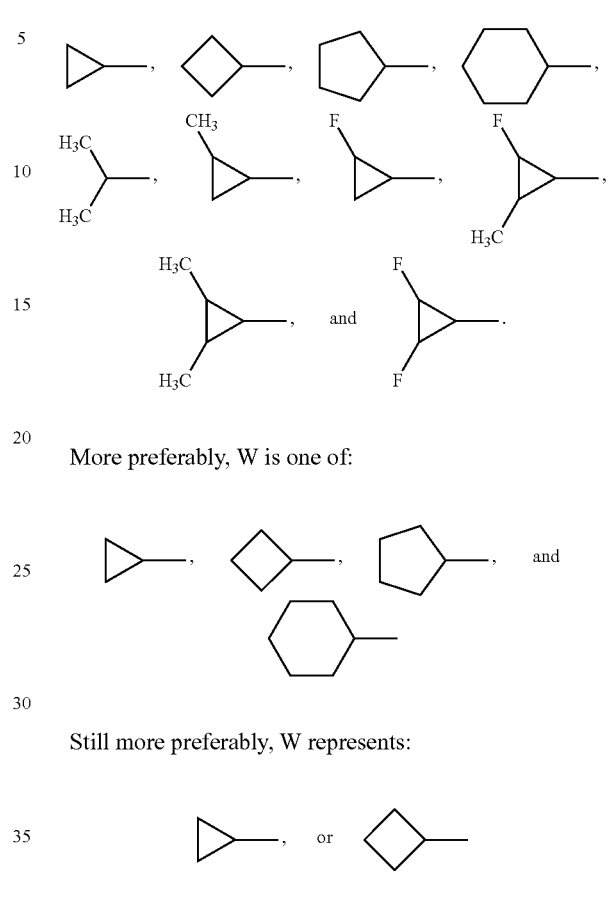

More preferably, W is one of:

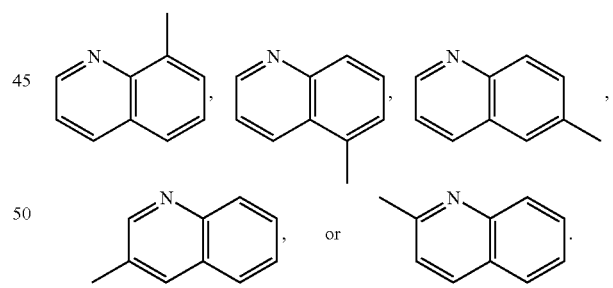

Still more preferably, W represents:

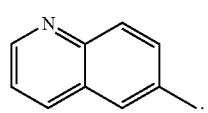

In one preferred embodiment, in the compound of the present invention having Formula A, Q represents:

More preferably, Q represents the following group:

In one preferred embodiment, in the compound of the present invention having Formula A, B, E, G, R, T, or M each independently represents a hydrogen, a fluorine, a methyl, a trifluoromethyl, a cyano, or an amino, especially a hydrogen.

In one preferred embodiment, in the compound of the present invention having Formula A, Y is a hydrogen.
The following specific compounds are particularly preferred:
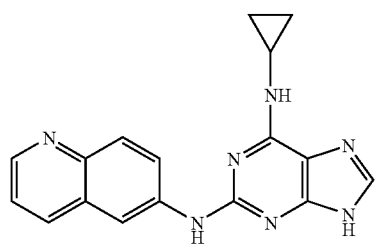
I
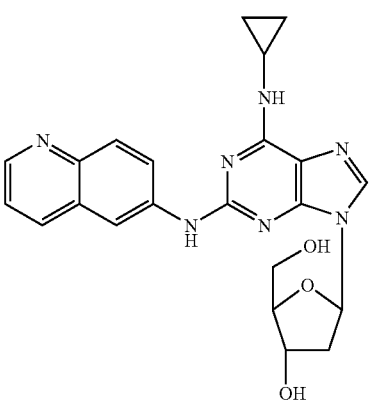
II
III
IV
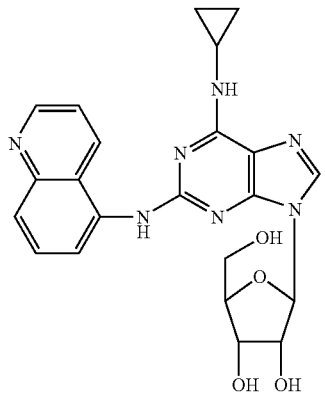
V
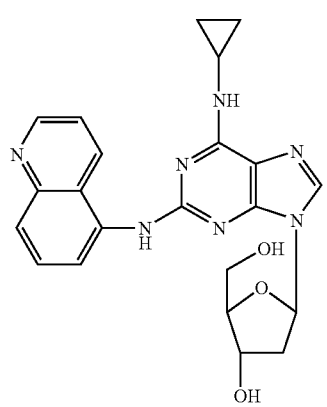
VI
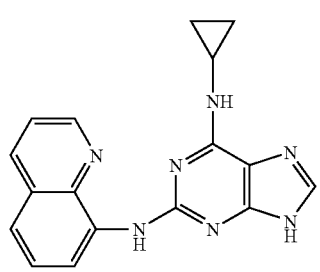
VII
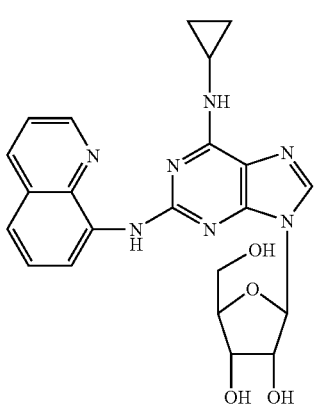
VIII

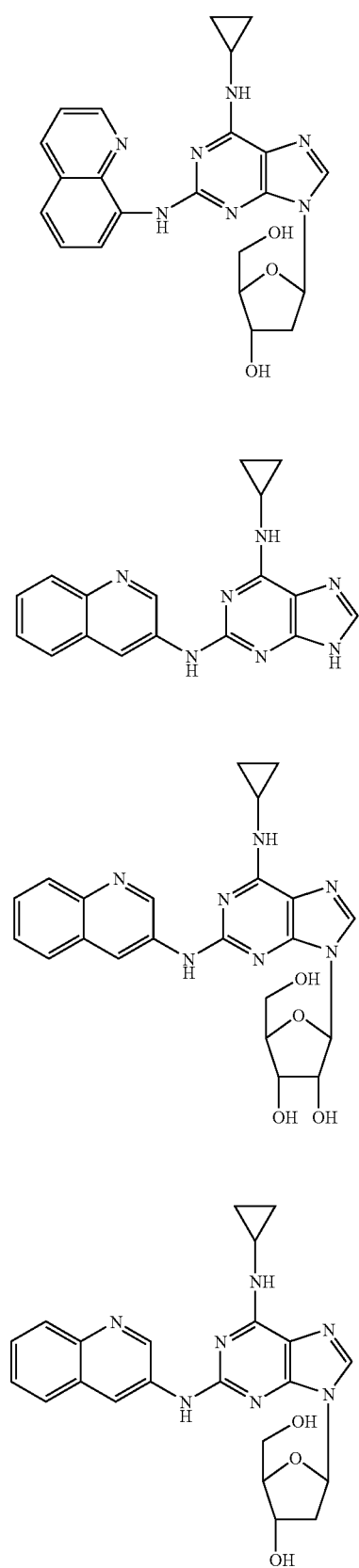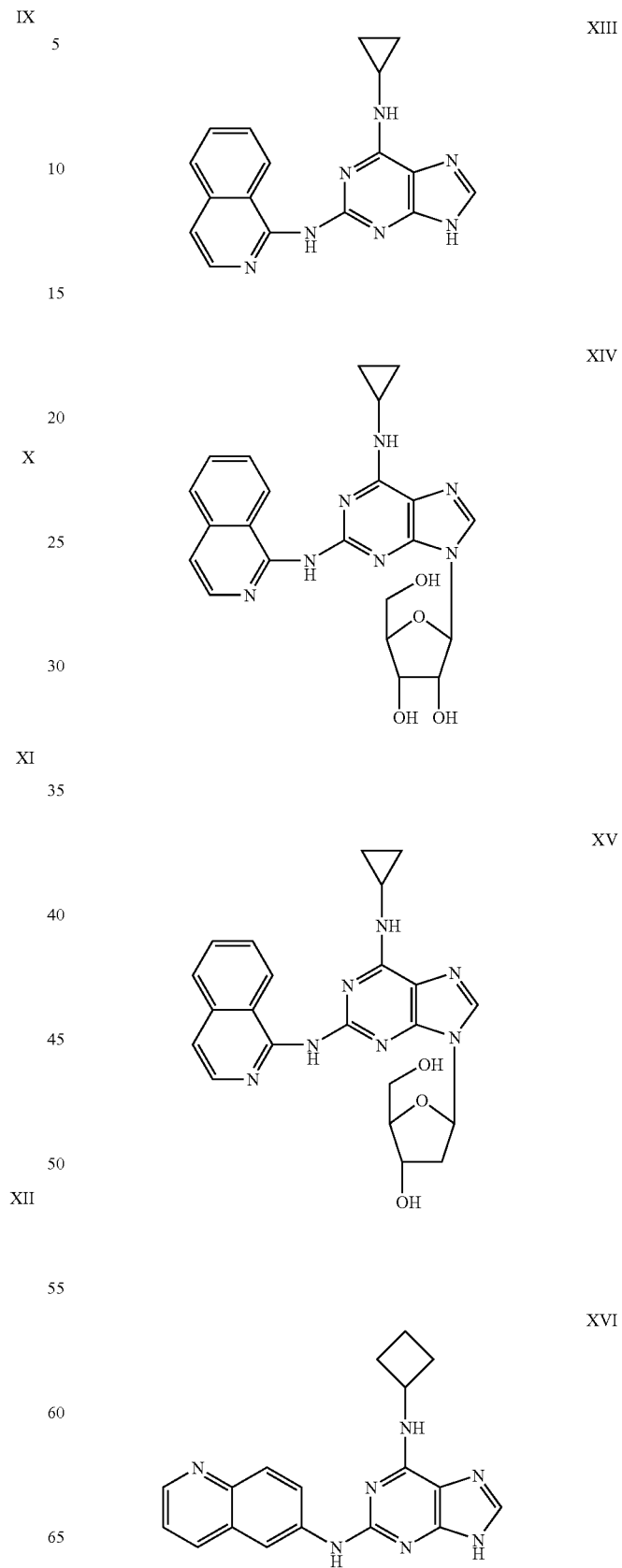

-continued

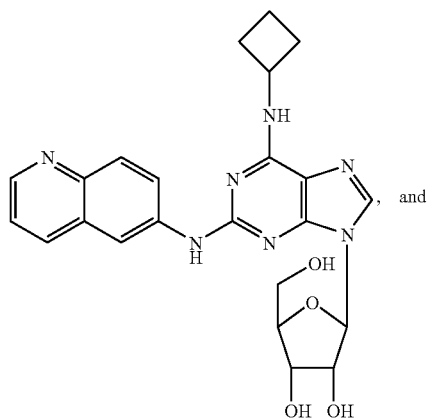
XVII and

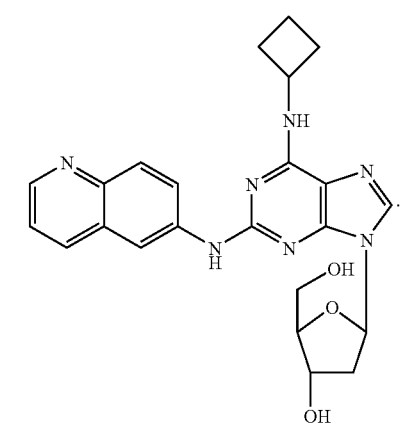
XVIII

Compound (I) is especially preferred:

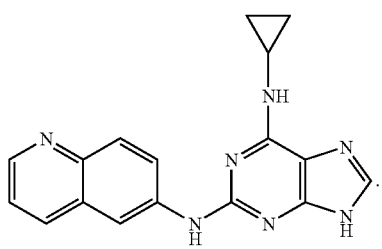
(I)

In a further embodiment, the present invention provides a library of compounds that comprises any compound described above, or its salt or its hydrate.

The present invention further provides with a process for the production of the above described compounds. In one embodiment, the compounds of this invention can be prepared in accordance with the following schemes:

(1) The reaction is carried out in the presence of (j) and Q—NH$_2$,

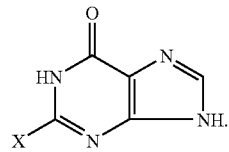
(j)

resulting in compound (b)

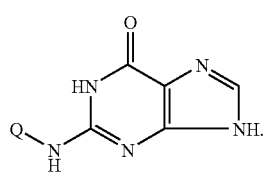
(b)

The above reaction is carried out in an organic solvent, in the presence of (j) and 0.8-1.5 mol/ml Q—NH$_2$, the mixture was heated at 50-150° C. for 1-72 hours, then water was added to the reaction mixture, and the reaction mixture was allowed to cool to room temperature.

(2) Preparation of compound (c)

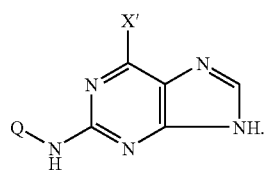
(c)

The reaction is carried out in an organic solvent, in the presence of compound (b) and a halogenating agent, the mixture was heated at 50-150° C. for 1-72 hours, cooled. Water was added and the pH of the mixture ph was adjusted to 2-5 with an acid, and was allowed to cool at room temperature.

(3) Preparation of compound (f)

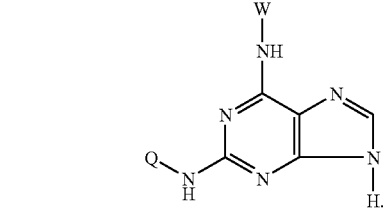
(f)

The reaction is carried out in an organic solvent, in the presence of compound (c), 0.8-1.5 mol/mol W—NH$_2$ and an acid acceptor, the mixture was heated at 50-150° C. for 1-72 hours. The solvent was then distilled off. Wherein X represents Br, X' represents Cl, W is as defined above.

According to another embodiment, the present invention also provides a process for the production of a suitable salt of the above mentioned compound.

In another embodiment, the compounds of this invention can be prepared in accordance with the following schemes:

(1) The reaction is carried out in the presence of (k) and W—NH₂,

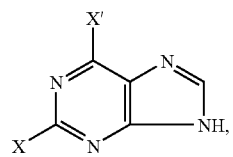

(k)

resulting in compound (e):

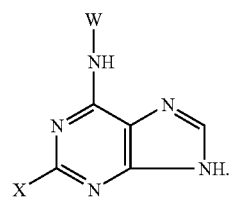

(e)

The reaction is carried out in an organic solvent, in the presence of compound (k), 0.8-1.5 mol/mol W—NH₂ and an acid acceptor, the mixture was heated at 30-150° C. for 1-72 hours. The solvent was then distilled off.

(2) Preparation of compound (f)

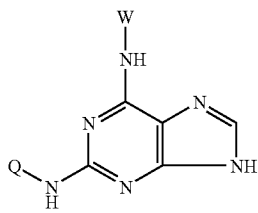

(f)

wherein X and X' represent Cl, and W is as defined above. The reaction is carried out in an organic solvent, in the presence of compound (e), 0.8-1.5 mol/mol Q—NH2, and an acid acceptor. The mixture was heated at 70-170° C. for 1-72 hours. The solvent was then distilled off.

The salt of the compound of Formula A can be any pharmaceutically acceptable salt, known to those skilled in the art. The salt of the compound can be synthesized by inorganic acid or organic acid, preferably as hydrochloride, hydrobromide, hydroiodate, p-toluenesulfonate, phosphate, sulphate, perchloride, acetate, trifluoroacetate, propionate, citrate, malonate, succinate, lactate, oxalate, tartrate, benzoate. The salt also can be that of a base, including an inorganic or organic base, such as magnesium hydroxide, calcium hydroxide, morpholine, piperidine, dimethylamine, diethylamine, etc.

In a preferred embodiment, the compounds of this invention are prepared in accordance with the following routines A and B:

Routine A:

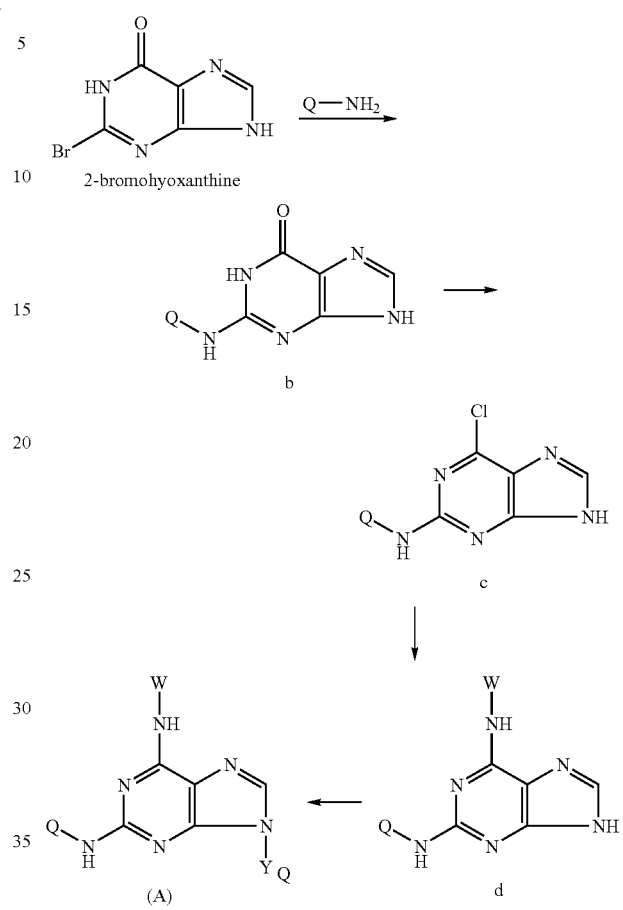

Routine B:

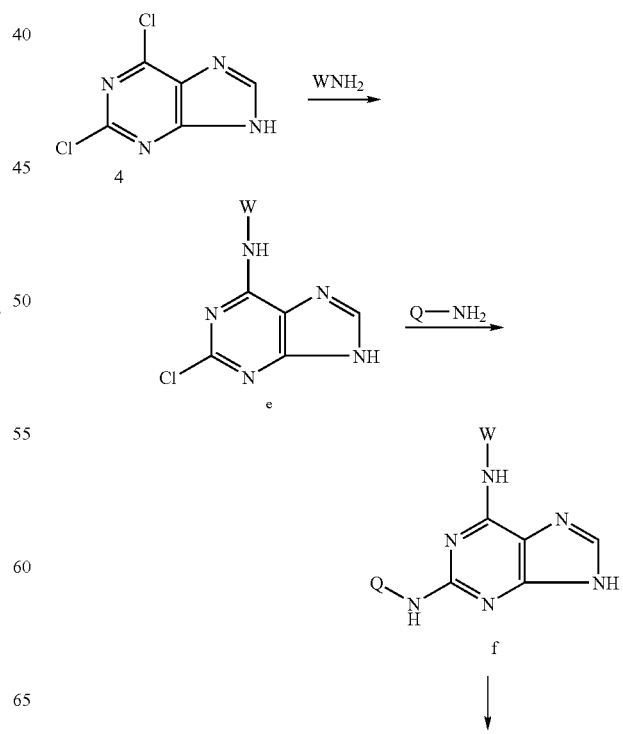

-continued

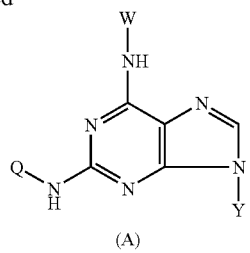

(A)

Compounds of the present invention have been found to specifically inhibit tumor cells (e.g. prostate cancer cell lines PC-3 and H-22) in a dose-dependent manner, and the growth of murine Lewis lung carcinoma in syngeneic C57B16/J mice. In addition, compounds of the present invention significantly inhibits the growth of H-22 liver cancer in a mouse model with no or low toxicity. The compounds of the present invention inhibit growth of primary tumor and their metastases. Accordingly, compounds of the present invention are useful for treating cancers when administered to a patient in need thereof.

In another embodiment, the present invention provides a pharmaceutical composition comprising a compound described above and a pharmaceutically acceptable adjuvant or excipient, and a method for treating cancer by administering an effective amount of the pharmaceutical composition to a patient in need thereof. Administration of an "effective amount" or a "therapeutically effective amount" of a compound of the present invention means an amount that is useful, at dosages and for periods of time necessary to achieve the desired result. The therapeutically effective amount of a compound in accordance with the present invention may vary according to factors, such as the disease state, age, sex, and weight of the subject. Dosage regimens in the patient may be adjusted to provide the optimum therapeutic response. For example, several divided doses may be administered daily or the dose may be proportionally reduced as indicated by the exigencies of the therapeutic situation. In the context of the present invention, a "pharmaceutically acceptable salt," refer to salts prepared from pharmaceutically acceptable, non-toxic acids.

The pharmaceutical compositions according to the invention can be present and administered as liquid, semi-solid or solid medicament forms and in the form of e.g. injection solutions, drops, juices, syrups, suspensions, sprays, granules, tablets, pellets, patches, capsules, plasters, suppositories, ointments, creams, lotions, gels, emulsions or aerosols, and comprise a compound of the present invention, and pharmaceutical auxiliary substances according to the galenical form, such as e.g. carrier materials, fillers, solvents, diluents, surface-active substances, dyestuffs, preservatives, disintegrating agents, anti-friction agents, lubricants, flavorings and/or binders. These auxiliary substances can be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatine, sorbitol, inositol, mannitol, microcrystalline cellulose, methylcellulose, carboxymethylcellulose, cellulose acetate, shellac, cetyl alcohol, polyvinylpyrrolidone, paraffins, waxes, naturally occurring and synthetic gums, acacia gum, alginates, dextran, saturated and unsaturated fatty acids, stearic acid, magnesium stearate, zinc stearate, glyceryl stearate, sodium lauryl sulfate, edible oils, sesame oil, coconut oil, ground nut oil, soya bean oil, lecithin, sodium lactate, polyoxyethylene and -propylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crosspovidone, agar and bentonite. The choice of auxiliary materials and the amounts thereof to be employed depend on whether the medicament is to be administered orally, perorally, subcutaneously, parenterally, intravenously, intraperitoneally, intradermally, intramuscularly, intranasally, buccally, rectally or locally, for example to infections on the skin, the mucous membranes and the eyes. Formulations in the form of tablets, coated tablets, capsules, granules, drops, juices and syrups are suitable, inter alia, for oral administration, and solutions, suspensions, easily reconstitutable dry formulations and sprays are suitable for parenteral, topical and inhalatory administration. A compound according to the invention in a depot in dissolved form or in a patch, optionally with the addition of agents which promote penetration through the skin, are suitable formulations for percutaneous administration. Formulation forms which can be used orally or percutaneously can release the compound according to the invention in a delayed or controlled manner.

The medicaments and pharmaceutical compositions according to the invention are prepared with the aid of agents, devices, methods and processes which are well-known in the prior art of pharmaceutical formulation, such as are described, for example, in Remington's Pharmaceutical Sciences, 18th ed., Mack Publishing Co., Easton, Pa. (1990), in particular in part 8, sections 76 to 93.

Thus for a solid formulation, such as a tablet, the active compound of the medicament, can be mixed with a pharmaceutical carrier, e.g. conventional tablet constituents, such as maize starch, lactose, sucrose, sorbitol, talc, magnesium stearate, dicalcium phosphate or gum, and pharmaceutical diluents, such as e.g. water, in order to form a solid preformulation composition which comprises a compound according to the invention or a pharmaceutically acceptable salt thereof in homogeneous distribution. Homogeneous distribution here is understood as meaning that the active compound is distributed uniformly over the entire preformulation composition, so that this can easily be divided into unit dose forms of the same action, such as tablets, pills or capsules. The solid preformulation composition is then divided into unit dose forms. The tablets or pills of the medicament according to the invention or of the compositions according to the invention can also be coated, or compounded in another manner in order to provide a dose form with delayed release. Suitable coating compositions are, inter alia, polymeric acids and mixtures of polymeric acids with materials such as e.g. shellac, cetyl alcohol and/or cellulose acetate.

The amount of active compound to be administered to the patient varies and depends on the weight, age and disease history of the patient, as well as on the mode of administration, the indication and the severity of the disease. A range of does, for example 0.1 to 5,000 mg/kg, in particular 1 to 500 mg/kg, preferably 2 to 250 mg/kg of body weight of a compound according to the invention are usually administered.

The pharmaceutical composition of the present invention may be administered enterally (such as orally or via rectal administration), externally, or parenterally e.g. via injection. Suitable formulations include tablets (such as conventional tablets, buccal tablets, sublingual tablet, oral cavity patch, chewable tablet, effervescent tablet, vaginal tablet, vaginal effervescent tablet, sustained-release tablet, controlled release tablet, enteric coated tablet, buccal rapid-release tablet), capsules (hard capsules, soft capsules, sustained-release capsules, controlled-release capsules, enteric-coated capsules, etc), pills (dripping pills, sugar coated pills, pellets), oral liquid (oral solution, oral suspension, oral emulsion, etc), granules (suspension granules, soluble granules, effervescent granules, gastro-resistant granules, sustained-release granules, controlled-release granules, etc), injection (injectable solution, injectable emulsion, injectable suspension), intravenous infusion, powder for injection, concentrated solution for injection, implants, etc, and other medicament form such as suppositories, aerosol, aerosol powder, spray, gel, pellicles, patches, etc.

Compounds of the present invention may be incorporated into biodegradable polymers allowing for sustained release of the compound, the polymers being implanted in the vicinity of where drug delivery is desired, for example, at the site of a tumor or implanted so that the compound is slowly released. The biodegradable polymers and their use are described, for example, in detail in Brem et al., J. Neurosurg. 74:441-446 (1991). Osmotic mini pumps may also be used to provide controlled delivery.

Toxicity and therapeutic efficacy of such compounds can be determined by standard pharmaceutical procedures in cell cultures or experimental animals, e.g., for determining the LD50 (the dose lethal to 50% of the population) and the ED50 (the dose the therapeutically effective in 50% of the population). The dose ratio between toxic and therapeutic effects is the therapeutic index and it can be expressed as the ratio LD50/ED50. Compounds which exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized.

Pharmaceutical composition of the present invention is suitable for treating cancers and the related diseases, and may be used alone or in combination with other anti-cancer drugs. An ordinarily skilled person in the art will be able to determine the suitable dosage for the treatment, depending on the types of disease to be treated, the formulation and the conditions of the patient.

The compounds of this invention can be used to prevent or treat abnormal cell proliferation, especially those found in tumors or cancers, including lung cancer, liver cancer, leucocythaemia, osteocarcinoma, pancreas cancer, skin cancer, melanoma, metrocarcinoma, oophoroma, rectal carcinoma, gastric carcinoma, colon cancer, breast carcinoma, salpinx carcinoma, endometrium carcinoma, cervix carcinoma, vagina carcinoma, carcinoma of vulva, esophagus carcinoma, small intestine carcinoma, incretion carcinoma, soft tissue sarcoma, urethra carcinoma, prostatic cancer, lymphocytoma, bladder cancer, nephridium cancer, tumors of vertebral column, tumors in the neuroglia of the brain, and pituitary adenoma.

EXAMPLES

The following EXAMPLES illustrate the present invention. Routines A and B illustrates the preparation of compounds I, II and III.

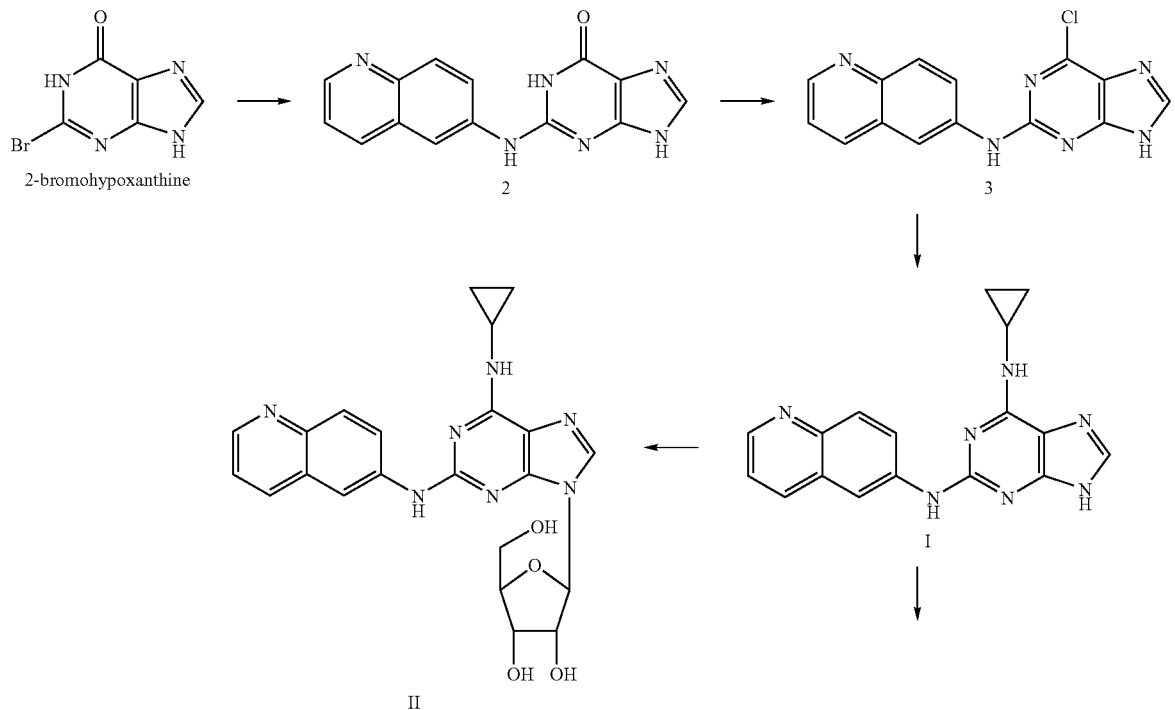

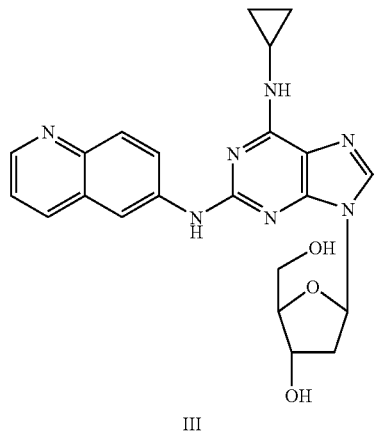

III

Example 1

Preparation of Compound I

1. In 200 ml water, 20 g (93 mmol) of 2-bromo-hypoxanthine, 13 g (90 mmol) of 6-aminoquinoline, 60 ml ethylene glycol monomethyl ether were mixed and the mixture was refluxed for 48 hours. The reaction mixture was then poured into ice-water, the solid was isolated by filtration, washed with 200 ml ammonia water and 50 ml methanol three times, and dried. The residue obtained was purified by column chromatography on silica gel to afford 14.2 g of compound 2.

2. 12 g (43 mmol) of compound 2, 150 ml phosphorus oxychloride, and 15 ml of N,N-xylidine were mixed and the mixture was refluxed for 30 minutes. The mixture was then cooled at room temperature for 2 hours. The reaction mixture was then poured into 2000 ml ice-water. The pH of mixture was adjusted to 3. The yellow solid was isolated by filtration. The residue obtained was purified by column chromatography on silica gel to afford 14.2 g of chloride 3.

3. 10 g (34 mmol) of chloride 3, 10 ml (145 mmol) of cyclopropylamine, 28 ml (200 mmol) of triethylamine, and 100 ml of DMF were mixed. The mixture was stirred at 100° C. for 3 hours. The solvent was then distilled off and the residue was dissolved with ethylene glycol dimethyl ether. The mixture was filtered, and the solvent of filtrate was distilled off and the residue obtained was purified by column chromatography on silica gel to afford 7 g compound I (mp>250° C.).

Compound I: HNMR (DMSO-d$_6$, δ): 0.640~0.642 (2Hs), 0.845~0.860(2H, m), 3.045 (1H, s), 7.0411~7.432 (1H, m), 7.632(1H, s, peak disappeared after added the heavy water), 7.865~7.888 (2H, m), 7.997~8.018 (1H, m), 8.116~8.136 (1H, m), 8.623~8.682 (2H, m), 9.242 (1H, s, peak disappeared after added the heavy water), 12.400 (1H, s, peak disappeared after added the heavy water). MS (ESI): 318 (M+H$^+$) 340 (M+Na$^+$).

Example 2

Preparation of Compound II 10 ml of anhydrous acetonitrile, 4.76 g (15 mmol) of compound I, and 6.3 ml (25 mmol) of N,O-Bis(trimethylsilyl)acetamide were mixed. The mixture was stirred at room temperature for 1 hour. 1.27 g of tetraacetyl ribofuranose, dissolved in 10 ml of acetonitrile and 1.10 ml of TMSTF, was then added to the mixture and was refluxed for 5 hours. 1.25 ml (5 mmol) of N,O-Bis(trimethylsilyl)acetamide was added to the mixture, and then stirred for 24 hours. The solvent was distilled off and the residue was dissolved with 20 ml of methanol. The reaction mixture was carried out in an atmosphere of ammonia gas for 2 hours. The solvent was distilled off. The residue obtained was purified column chromatography on silica gel to afford 4.65 g of compound II.

Compound II: MS (ESI): 450 (M+H$^+$), 472 (M+Na$^+$).

Example 3

Preparation of Compound III 10 g (31.5 mmol) of compound I, 1.5 g of 60% NaH, and 150 ml of anhydrous acetonitrile were mixed. The mixture was stirred for 30 minutes in an atmosphere of nitrogen. 12 g of 3,5-diparatoluensulfonyl-2-deoxy-β-D-ribofuranose-1-chloride was added to the mixture in 20 minutes. The mixture was stirred at room temperature for 2 hours. The mixture was filtered, and the solvent of the filtrate was distilled off. The oil residue was purified by column chromatography on silica gel to afford 9.8 g of 2-(6-aminoquinolyl)-6-cyclopropyl-9-(3,5-diparatoluensulfonyl-2-deoxy-β-D-ribofuranose) purine.

The above product was added to 25 mmol of sodium methoxide and 400 ml of methanol. The mixture was stirred at room temperature for 5 hours. The pH of the mixture was adjusted to 7 with acetic acid. The solvent was distilled off and the residue obtained was purified by column chromatography on silica gel to afford 5 g of compound III.

Compound III: 434 (M+H$^+$), 456(M+Na$^+$).

Example 4

Preparation of Compound I According to Routine B

Routine B:

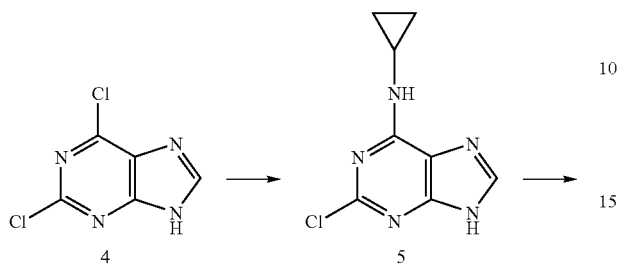

4                    5

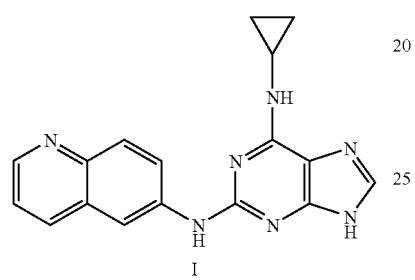

I 1. 3.78 g (20 mmol) of dichloropurine 4, 20 ml of DMF, 1.4 ml of cyclopropylamine, and 3.08 ml of triethylamine were mixed. The mixture was stirred at 80° C. for 5 hours. The solvent was distilled off and the residue obtained was purified by column chromatography on silica gel to afford 3.34 g of compound 5.

2. 2.99 g (14.3 mmol) of compound 5, 5.1 g (36.1 mmol) of 6-amino-quinoline, 50 ml of DMF, and 2.4 ml of triethylamine were mixed. The mixture was refluxed at 140° C. for 72 hours. The solvent was distilled off. The residue obtained was purified by column chromatography on silica gel to afford 3.54 g of compound I Examples 5-7 illustrate the preparation of compounds IV, V, and VI.

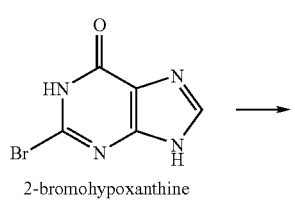

2-bromohypoxanthine

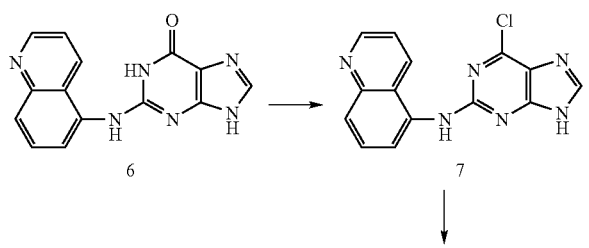

6                    7

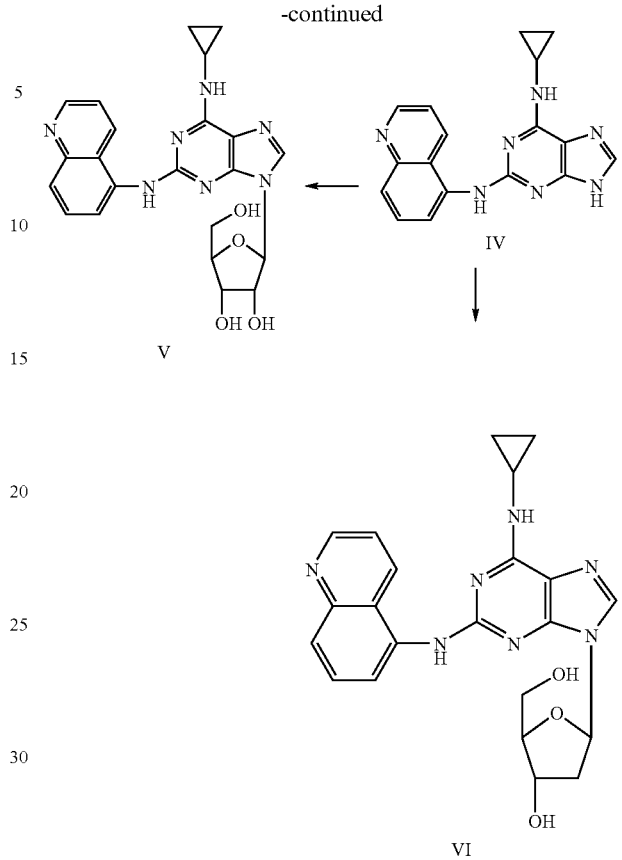

Example 5

Preparation of Compound IV

1. In 200 ml water, 20 g (93 mmol) of 2-bromo-hypoxanthine, 13 g (90 mmol) of 5-aminoquinoline, and 60 ml ethylene glycol monomethyl ether were mixed and the mixture was refluxed for 48 hours. The reaction mixture was then poured into ice-water, and the solid was isolated by filtration, washed with 200 ml ammonia water and 50 ml methanol three times, and dried. The residue obtained was purified by column chromatography on silica gel to afford 8 g of compound 6.

2. 12 g (43 mmol) of compound 6, 150 ml phosphorus oxychloride, and 15 ml of N,N-xylidine were mixed and the mixture was refluxed for 30 minutes. The mixture was then cooled at room temperature for 2 hours. The reaction mixture was then poured into 2000 ml ice-water. The pH of mixture was adjusted to 3. The yellow solid was isolated by filtration. The residue obtained was purified by column chromatography on silica gel to afford 12.0 g of chloride 7.

3. 10 g (34 mmol) of chloride 7, 10 ml (145 mmol) of cyclopropylamine, 28 ml (200 mmol) of triethylamine, and 100 ml of DMF were mixed. The mixture was stirred at 100° C. for 3 hours. The solvent was then distilled off and the residue was dissolved with ethylene glycol dimethyl ether. The mixture was filtered, and the solvent of filtrate was distilled off and the residue obtained was purified by column chromatography on silica gel to afford 9 g compound IV.

Compound IV: MS (ESI): 318 (M+H⁺), 340(M+Na⁺)

Example 6

Preparation of Compound V 10 ml of anhydrous acetonitrile, 4.76 g (15 mmol) of compound IV, and 6.3 ml (25 mmol) of N,O-Bis(trimethylsilyl)acetamide were mixed. The mixture was stirred at room temperature for 1 hour. 1.27 g of tetraacetyl ribofuranose dissolved in 10 ml of acetonitrile and 1.10 ml of TMSTF was then added to the mixture and was refluxed for 5 hours. 1.25 ml (5 mmol) of N,O-Bis(trimethylsilyl)acetamide was added to the mixture, and then stirred for 24 hours. The solvent was distilled off and the residue was dissolved with 20 ml of methanol. The reaction mixture was carried out in an atmosphere of ammonia gas for 2 hours. The solvent was distilled off. The residue obtained was purified column chromatography on silica gel to afford 4.07 of compound V.

Example 7

Preparation of Compound VI 10 g (31.5 mmol) of compound IV, 1.5 g of 60% NaH, and 150 ml of anhydrous acetonitrile were mixed. The mixture was stirred for 30 minutes in an atmosphere of nitrogen. 12 g of 3,5-diparatoluensulfonyl-2-deoxy-β-D-ribofuranose-1-chloride was added to the mixture in 20 minutes. The mixture was stirred at room temperature for 2 hours. The mixture was filtered, and the solvent of the filtrate was distilled off. The oil residue was purified by column chromatography on silica gel to afford 8.0 g of 2-(5-aminoquinolyl)-6-cyclopropyl-9-(3,5-diparatoluensulfonyl-2-deoxy-β-D-ribofuranose) purine.

The above product was added to 25 mmol of sodium methoxide and 400 ml of methanol. The mixture was stirred at room temperature for 5 hours. The pH of mixture was adjusted to 7 with acetic acid. The solvent was distilled off and the residue obtained was purified by column chromatography on silica gel to afford 5.75 g of compound VI.

Compound VI: MS (ESI): 434 (M+H⁺), 456 (M+Na⁺)

Example 8

Preparation of Compound IV, Alternative to Example 5

The process of preparation of Compound IV was as follows:

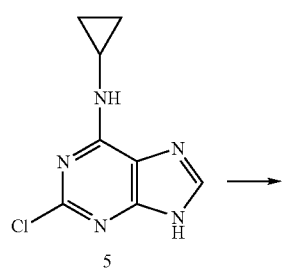

5

-continued

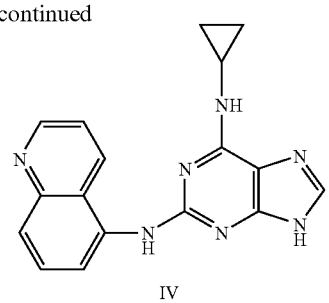

IV 2.99 g (14.3 mmol) of compound 5, 5.1 g (36.1 mmol) of 5-amino-quinoline, and 50 ml of DMF, 2.4 ml of triethylamine were mixed. The mixture was refluxed at 140° C. for 72 hours. The solvent was distilled off. The residue obtained was purified by column chromatography on silica gel to afford 2.88 g of compound IV.

Examples 9-11 illustrate the preparation of compounds VII, VIII and IX.

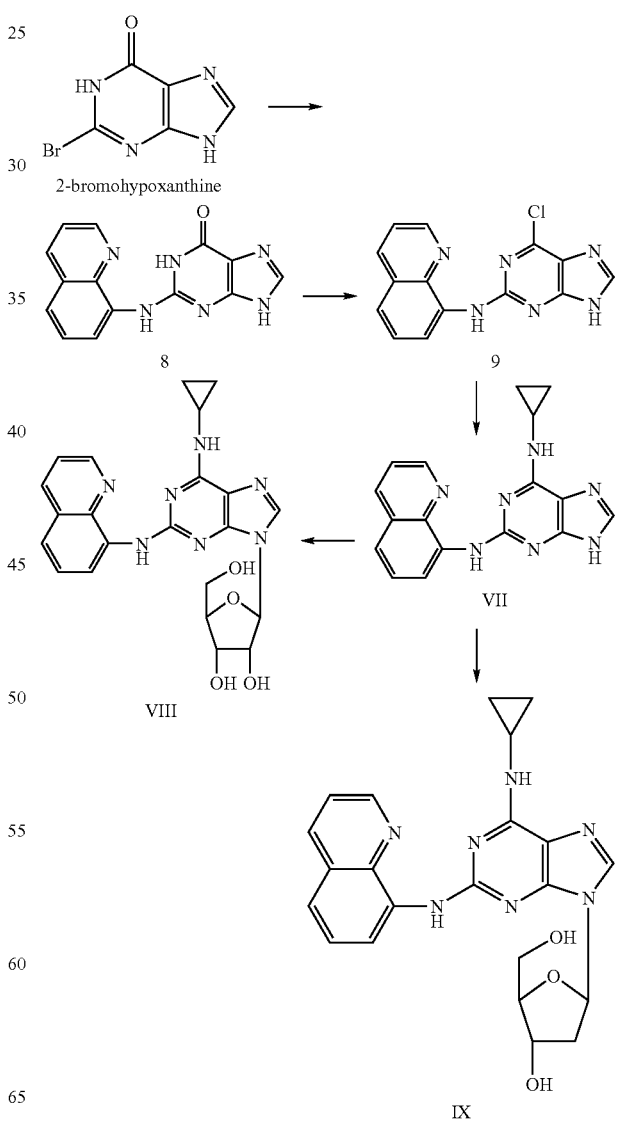

Example 9

Preparation of Compound VII

1. In 200 ml water, 20 g (93 mmol) of 2-bromo-hypoxanthine, 13 g (90 mmol) of 8-aminoquinoline, and 60 ml ethylene glycol monomethyl ether were mixed and the mixture was refluxed for 48 hours. The reaction mixture was then poured into ice-water, the solid was isolated by filtration, washed with 200 ml ammonia water and 50 ml methanol three times, and dried. The residue obtained was purified by column chromatography on silica gel to afford 11.4 g of compound 8

2. 12 g (43 mmol) of compound 8, 150 ml of phosphorus oxychloride, and 15 ml of N,N-xylidine were mixed and the mixture was refluxed for 30 minutes. The mixture was then cooled at room temperature for 2 hours. The reaction mixture was then poured into 2000 ml ice-water. The pH of mixture was adjusted to 3. The yellow solid was isolated by filtration. The residue obtained was purified by column chromatography on silica gel to afford 10.3 g of chloride 9.

3. 10 g (34 mmol) of chloride 9, 10 ml (145 mmol) of cyclopropylamine, 28 ml (200 mmol) of triethylamine, and 100 ml of DMF were mixed. The mixture was stirred at 100° C. for 3 hours. The solvent was then distilled off and the residue was dissolved with ethylene glycol dimethyl ether. The mixture was filtered, and the solvent of filtrate was distilled off and the residue obtained was purified by column chromatography on silica gel to afford 6 g compound VII.

Compound VII: MS (ESI):318 (M+H$^+$), 340 (M+Na$^+$)

Example 10

Preparation of Compound VIII 10 ml of anhydrous acetonitrile, 4.76 g (15 mmol) of compound VII, and 6.3 ml (25 mmol) of N,O-Bis(trimethylsilyl)acetamide were mixed. The mixture was stirred at room temperature for 1 hour. 1.27 g of tetraacetyl ribofuranose, dissolved in 10 ml of acetonitrile and 1.10 ml of TMSTF was then added to the mixed and was refluxed for 5 hours. 1.25 ml (5 mmol) of N,O-Bis(trimethylsilyl)acetamide was added to the mixture, and then stirred for 24 hours. The solvent was distilled off and the residue was dissolved with 20 ml of methanol. The reaction mixture was carried out in an atmosphere of ammonia gas for 2 hours. The solvent was distilled off. The residue obtained was purified column chromatography on silica gel to afford 4.2 g of compound VIII.

Compound VIII: MS (ESI): 450 (M+H$^+$), 472(M+Na$^+$),

Example 11

Preparation of Compound IX 10 g (31.5 mmol) of compound VII, 1.5 g of 60% NaH, and 150 ml of anhydrous acetonitrile were mixed. The mixture was stirred for 30 minutes in an atmosphere of nitrogen. 12 g of 3,5-diparatoluensulfonyl-2-deoxy-β-D-ribofuranose-1-chloride was added to the mixture in 20 minutes. The mixture was stirred at room temperature for 2 hours. The mixture was filtered, and the solvent of the filtrate was distilled off. The oil residue was purified by column chromatography on silica gel to afford 7.4 g of 2-(8-aminoquinolyl)-6-cyclopropyl-9-(3,5-diparatoluensulfonyl-2-deoxy-β-D-ribofuranose) purine.

The above product was added to 25 mmol of sodium methoxide and 400 ml of methanol. The mixture was stirred at room temperature for 5 hours. The pH of mixture was adjusted to 7 with acetic acid. The solvent was distilled off and the residue obtained was purified by column chromatography on silica gel to afford 3.2 g of compound IX.

Compound IX: MS (ESI): 434 (M+H$^+$), 456 (M+Na$^+$).

Example 12

Preparation of Compound VII; Alternative to Example 9

The process of preparation of compound was as follows:

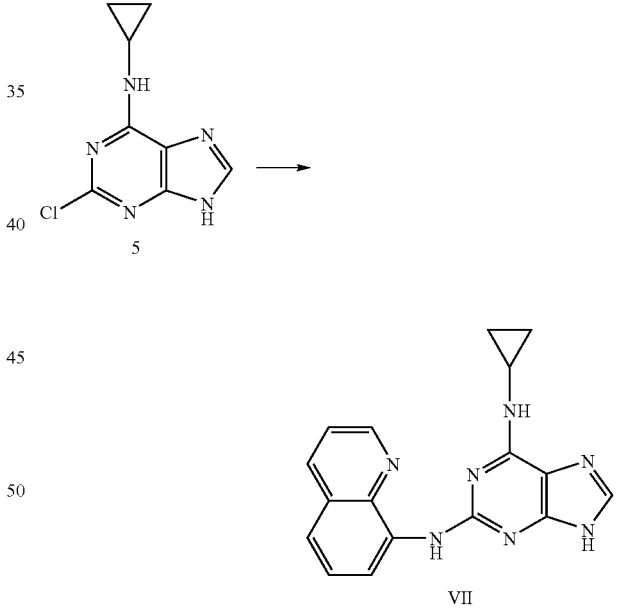

2.99 (14.3 mmol) of compound 5, 5.1 g (36.1 mmol) of 8-amino-quinoline, 50 ml of DMF, and 2.4 ml of triethylamine were mixed. The mixture was refluxed at 140° C. for 72 hours. The solvent was distilled off. The residue obtained was purified by column chromatography on silica gel to afford 4.10 g of compound VII.

Examples 13-15 illustrate the preparation of compounds X, XI and XII.

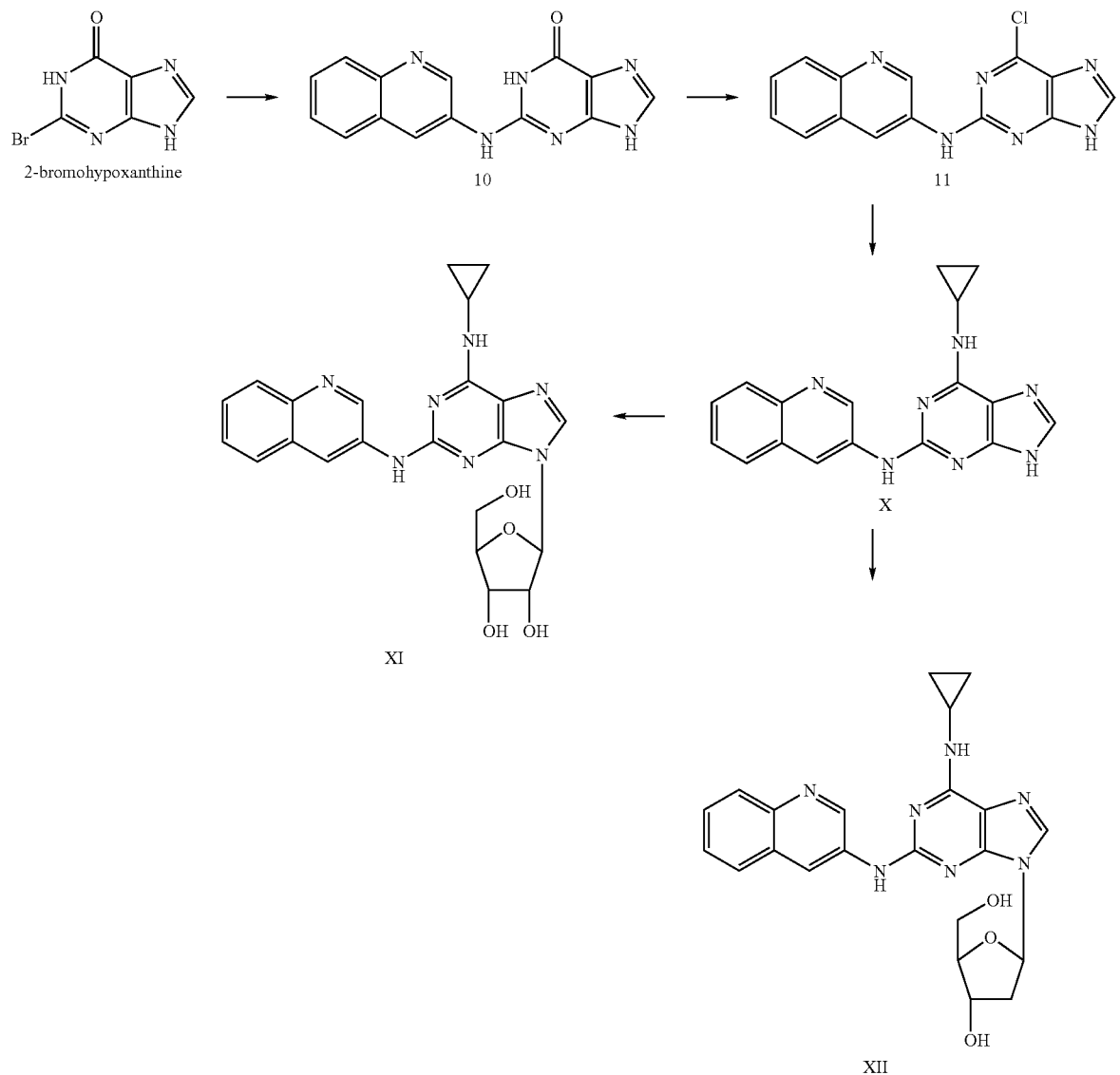

Example 13

Preparation of Compound X

1. In 200 ml water, 20 g (93 mmol) of 2-bromo-hypoxanthine, 13 g (90 mmol) of 3-aminoquinoline, and 60 ml ethylene glycol monomethyl ether were mixed and the mixture was refluxed for 48 hours. The reaction mixture was then poured into ice-water, the solid was isolated by filtration, washed with 200 ml ammonia water and 50 ml methanol three times, and dried. The residue obtained was purified by column chromatography on silica gel to afford 15.0 g of compound 10.

2. 12 g (43 mmol) of compound 10, 150 ml phosphorus oxychloride, and 15 ml of N,N-xylidine were mixed and the mixture was refluxed for 30 minutes. The mixture was then cooled at room temperature for 2 hours. The reaction mixture was then poured into 2,000 ml ice-water. The pH of mixture was adjusted to 3. The yellow solid was isolated by filtration. The residue obtained was purified by column chromatography on silica gel to afford 10.9 g of chloride 11.

3. 10 g (34 mmol) of chloride 11, 10 ml (145 mmol) of cyclopropylamine, 28 ml (200 mmol) of triethylamine, 100 ml of DMF were mixed. The mixture was stirred at 100° C. for 3 hours. The solvent was then distilled off and the residue was dissolved with ethylene glycol dimethyl ether. The mixture was filtered, and the solvent of filtrate was distilled off and the residue obtained was purified by column chromatography on silica gel to afford 10.1 g compound X (recovery rate 94%).

Compound X: MS (ESI): 318 (M+H$^+$), 340 (M+Na$^+$).

Example 14

Preparation of Compound XI 10 ml of anhydrous acetonitrile, 4.76 g (15 mmol) of compound X, and 6.3 ml (25 mmol) of N,O-Bis(trimethylsilyl)acetamide were mixed. The mixture was stirred at room temperature for 1 hour. 1.27 g of tetraacetyl ribofuranose, dissolved in 10 ml of acetonitrile and 1.10 ml of TMSTF was then added to the mixture and was refluxed for 5 hours. 1.25 ml (5 mmol) of N,O-Bis(trimethylsilyl) acetamide was added to the mixture, and then stirred for 24 hours. The solvent was distilled off and the residue was dissolved with 20 ml of methanol. The reaction mixture was carried out in an atmosphere of ammonia gas for 2 hours. The solvent was distilled off. The residue obtained was purified column chromatography on silica gel to afford 4.97 g of compound XI.

Compound XI: MS (ESI): 450 (M+H$^+$), 472 (M+Na$^+$).

Example 15

Preparation of Compound XII 10 g (31.5 mmol) of compound X, 1.5 g of 60% NaH, and 150 ml of anhydrous acetonitrile were mixed. The mixture was stirred for 30 minutes in an atmosphere of nitrogen. 12 g of 3,5-diparatoluensulfonyl-2-deoxy-β-D-ribofuranose-1-chloride was added to the mixture in 20 minutes. The mixture was stirred at room temperature for 2 hours. The mixture was filtered, and the solvent of the filtrate was distilled off. The oil residue was purified by column chromatography on silica gel to afford 8.8 g of 2-(3-aminoquinolyl)-6-cyclopropyl-9-(3,5-diparatoluensulfonyl-2-deoxy-β-D-ribofuranose) purine.

The above product was added to 25 mmol of sodium methoxide and 400 ml of methanol. The mixture was stirred at room temperature for 5 hours. The pH of mixture was adjusted to 7 with acetic acid. The solvent was distilled off and the residue obtained was purified by column chromatography on silica gel to afford 5.06 g of compound XII.

Compound XII: MS (ESI): 434 (M+H$^+$), 456 (M+Na$^+$).

Example 16

Preparation of Compound X, Alternative to Example 9

The process of preparation of compound was as follows:

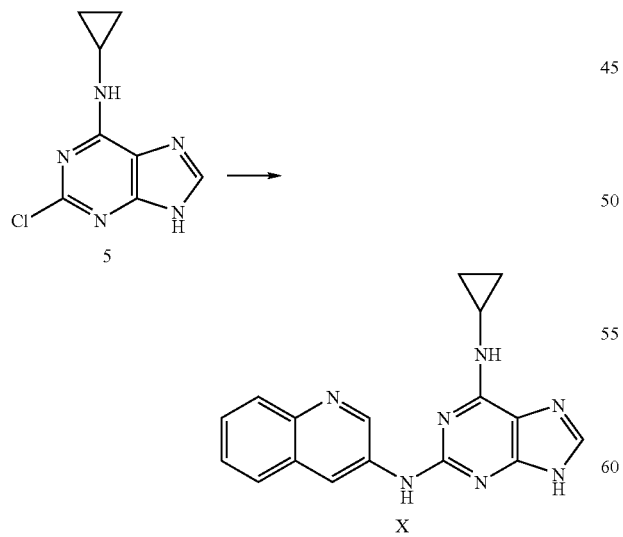

2.99 g (14.3 mmol) of compound 5, 5.1 g (36.1 mmol) of 3-amino-quinoline, 50 ml of DMF, and 2.4 ml of triethylamine were mixed. The mixture was refluxed at 140° C. for 72 hours. The solvent was distilled off. The residue obtained was purified by column chromatography on silica gel to afford 3.54 g of compound X.

Examples 17-19 illustrate the preparation of compounds VII, XIV, and XV.

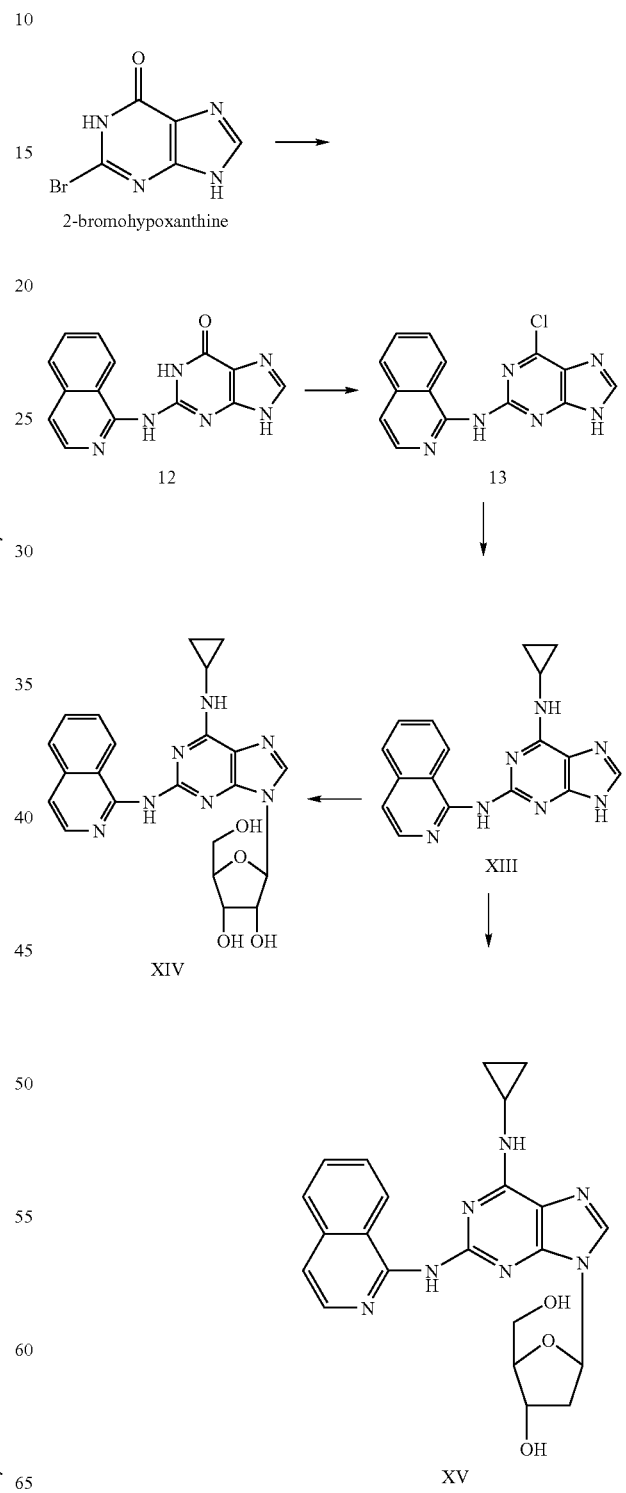

Example 17

Preparation of Compound XIII

1. In 200 ml water, 20 g (93 mmol) of 2-bromo-hypoxanthine, 13 g (90 mmol) of 1-aminoquinoline, and 60 ml ethylene glycol monomethyl ether were mixed and the mixture was refluxed for 48 hours. The reaction mixture was then poured into ice-water, the solid was isolated by filtration, washed with 200 ml ammonia water and 50 ml methanol three times, dried. The residue obtained was purified by column chromatography on silica gel to afford 14.2 g of compound 12.

2. 12 g (43 mmol) of compound 12, 150 ml phosphorus oxychloride, 15 ml of N,N-xylidine were mixed and the mixture was refluxed for 30 minutes. The mixture was then cooled at room temperature for 2 hours. The reaction mixture was then poured into 2000 ml ice-water. The pH of mixture was adjusted to 3. The yellow solid was isolated by filtration. The residue obtained was purified by column chromatography on silica gel to afford 11.5 g of chloride 13.

3. 10 g (34 mmol) of chloride 13, 10 ml (145 mmol) of cyclopropylamine, 28 ml (200 mmol) of triethylamine, and 100 ml of DMF were mixed. The mixture was stirred at 100° C. for 3 hours. The solvent was then distilled off and the residue was dissolved with ethylene glycol dimethyl ether. The mixture was filtered, and the solvent of filtrate was distilled off and the residue obtained was purified by column chromatography on silica gel to afford 4.2 g compound XIII.

Compound XIII: MS (ESI): 318 (M+H$^+$), 340 (M+Na$^+$).

Example 18

Preparation of Compound XIV 10 ml of anhydrous acetonitrile, 4.76 g (15 mmol) of compound XIII, and 6.3 ml (25 mmol) of N,O-Bis(trimethylsilyl)acetamide were mixed. The mixture was stirred at room temperature for 1 hour. 1.27 g of tetraacetyl ribofuranose, dissolved in 10 ml of acetonitrile, and 1.10 ml of TMSTF was then added to the mixture and was refluxed for 5 hours. 1.25 ml (5 mmol) of N,O-Bis(trimethylsilyl) acetamide was added to the mixture, and then stirred for 24 hours. The solvent was distilled off and the residue was dissolved with 20 ml of methanol. The reaction mixture was carried out in an atmosphere of ammonia gas for 2 hours. The solvent was distilled off. The residue obtained was purified column chromatography on silica gel to afford 4.2 g of compound XIV.

Compound XIV: MS (ESI): 450 (M+H$^+$), 472 (M+Na$^+$).

Example 19

Preparation of Compound XV 10 g (31.5 mmol) of compound XIII, 1.5 g of 60% NaH, and 150 ml of anhydrous acetonitrile were mixed. The mixture was stirred for 30 minutes in an atmosphere of nitrogen. 12 g of 3,5-diparatoluensulfonyl-2-deoxy-β-D-ribofuranose-1-chloride was added to the mixture in 20 minutes. The mixture was stirred at room temperature for 2 hours. The mixture was filtered, and the solvent of the filtrate was distilled off. The oil residue was purified by column chromatography on silica gel to afford 7.09 g of 2-(1-aminoquinolyl)-6-cyclopropyl-9-(3,5-diparatoluensulfonyl-2-deoxy-β-D-ribofuranose) purine.

The above product was added to 25 mmol of sodium methoxide and 400 ml of methanol. The mixture was stirred at room temperature for 5 hours. The pH of mixture was adjusted to 7 with acetic acid. The solvent was distilled off and the residue obtained was purified by column chromatography on silica gel to afford 3.8 g of compound XV.

Compound XV: MS (ESI): 434 (M+H$^+$), 456 (M+Na$^+$).

Example 20

Preparation of Compound XIII, Alternative to Example 17

The process of preparation of compound was as follows:

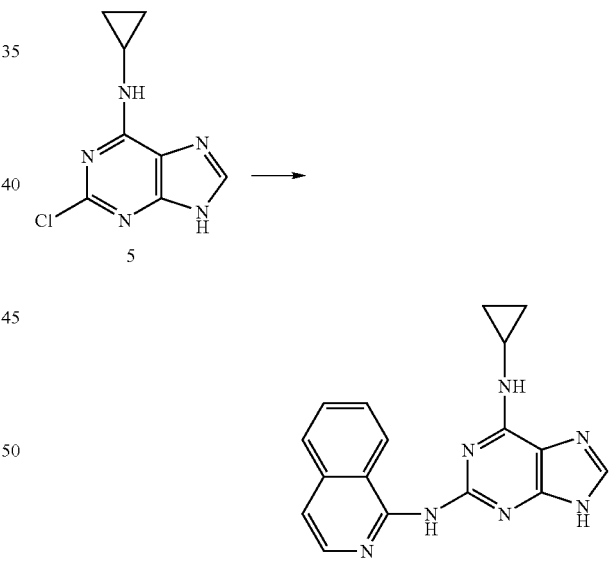

2.99 g (14.3 mmol) of compound 5, 5.1 g (36.1 mmol) of 1-amino-quinoline, 50 ml of DMF, and 2.4 ml of triethylamine were mixed. The mixture was refluxed at 140° C. for 72 hours. The solvent was distilled off. The residue obtained was purified by column chromatography on silica gel to afford 4.16 g of compound XIII.

Examples 21-22 illustrate the preparation of compound XVI, XVII, and XVIII.

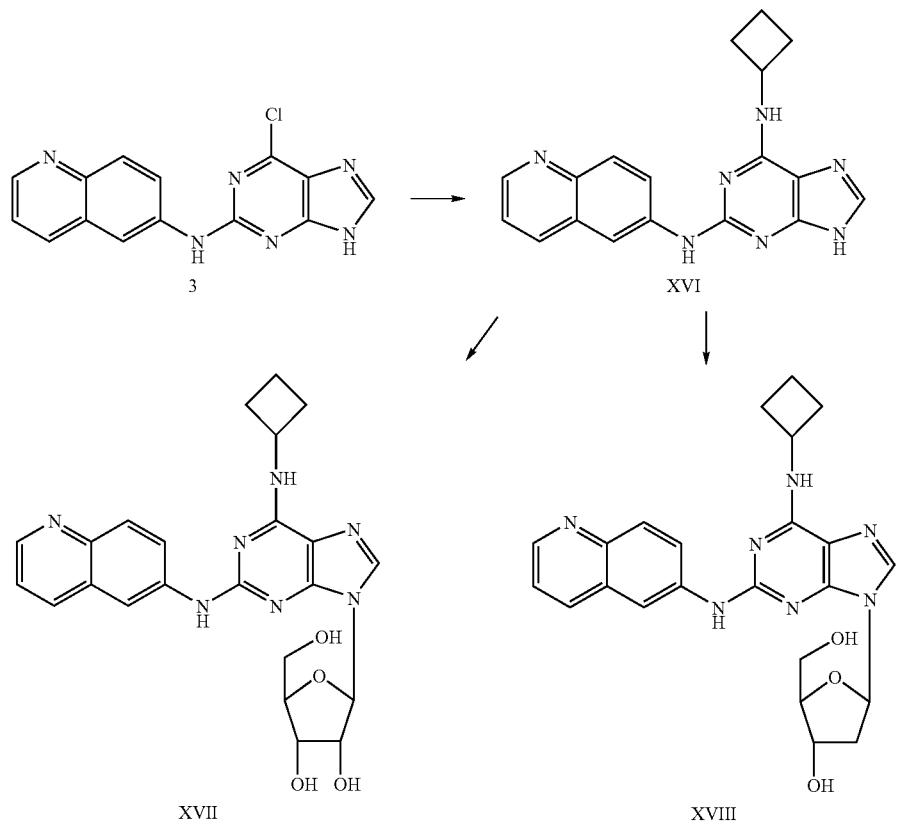

Example 21

Preparation of Compound XVI 10 g (34 mmol) of compound 3, 10 ml (145 mmol) of cyclobutylamine, 28 ml (200 mmol) of triethylamine, and 100 ml of DMF were mixed. The mixture was stirred at 100° C. for 3 hours. The solvent was then distilled off and the residue was dissolved with ethylene glycol dimethyl ether. The mixture was filtered, and the solvent of filtrate was distilled off and the residue obtained was purified by column chromatography on silica gel to afford 6.8 g compound XVI.

Compound XVI: MS (ESI): 332 (M+H$^+$), 354 (M+Na$^+$).

Example 22

Preparation of Compound XVII 10 ml of anhydrous acetonitrile, 4.76 g (15 mmol) of compound XVI, and 6.3 ml (25 mmol) of N,O-Bis(trimethylsilyl)acetamide were mixed. The mixture was stirred at room temperature for 1 hour. 1.27 g of tetraacetyl ribofuranose, dissolved in 10 ml of acetonitrile and 1.10 ml of TMSTF were then added to the mixture and refluxed for 5 hours. 1.25 ml (5 mmol) of N,O-Bis(trimethylsilyl)acetamide was added to the mixture, and then stirred for 24 hours. The solvent was distilled off and the residue was dissolved with 20 ml of methanol. The reaction mixture was carried out in an atmosphere of ammonia gas for 2 hours. The solvent was distilled off. The residue obtained was purified column chromatography on silica gel to afford 4.71 g of compound XVII.

Compound XVII: MS (ESI): 464 (M+H$^+$), 486 (M+Na$^+$).

Example 23

Preparation of Compound XVIII 10 g (31.5 mmol) of compound XVI, 1.5 g of 60% NaH, and 150 ml of anhydrous acetonitrile were mixed. The mixture was stirred for 30 minutes in an atmosphere of nitrogen. 12 g of 3,5-diparatoluensulfonyl-2-deoxy-β-D-ribofuranose-1-chloride was added to the mixture in 20 minutes. The mixture was stirred at room temperature for 2 hours. The mixture was filtered, and the solvent of the filtrate was distilled off. The oil residue was purified by column chromatography on silica gel to afford 2-(6-aminoquinolyl)-6-cyclobutyl-9-(3,5-diparatoluensulfonyl-2-deoxy-β-D-ribofuranose) purine.

The above product was added to 25 mmol of sodium methoxide and 400 ml of methanol. The mixture was stirred at room temperature for 5 hours. The pH of mixture was adjusted to 7 with acetic acid. The solvent was distilled off and the residue obtained was purified by column chromatography on silica gel to afford 7 g of compound XVIII.

Compound XVIII: MS (ESI): 448 (M+H$^+$), 470 (M+Na$^+$).

Example 24

Preparation of Compound XVI

The process of preparation of compound was as follows:

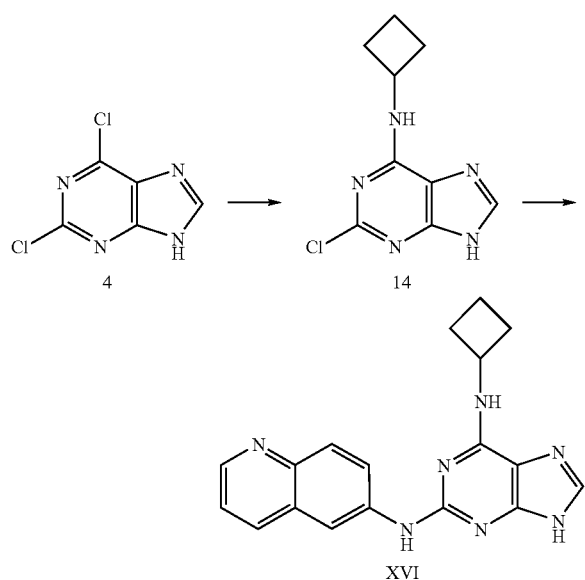

1. 3.78 g (20 mmol) of dichloropurine 4, 20 ml of DMF, 1.4 ml of cyclobutylamine, and 3.08 ml of triethylamine were mixed. The mixture was stirred at 80° C. for 5 hours. The solvent was distilled off and the residue obtained was purified by column chromatography on silica gel to afford 4.1 g of compound 14.

2. 2.99 g (14.3 mmol) of compound 14, 5.1 g (36.1 mmol) of 6-amino-quinoline, 50 ml of DMF, and 2.4 ml of triethylamine were mixed. The mixture was refluxed at 140° C. for 72 hours. The solvent was distilled off. The residue obtained was purified by column chromatography on silica gel to afford 3.82 g of compound XVI.

Example 25

Preparation of Hydrochloride and Lactate of Compound I

Preparation of the hydrochloride of compound I:

10 g of compound I, 210 ml of ethanol, and 25 ml of water were mixed. The mixture was heated to dissolve compound I. 0.7 ml of 2 mol/L HCl was added to the mixture. The mixture was refluxed for 0.5 hour. The mixture was allowed to cool at room temperature, and then was allowed to cool to below 5° C. for 5 hours. The pale yellow solid was isolated by filtration. The pale yellow solid was 10 g after dried. The melting point of the pale yellow solid was above 270° C.

Preparation of the lactate of compound I:

5 g of compound I, 105 ml of 95% ethanol, and 12.5 ml of water were mixed. The mixture was heated to dissolve compound I. 10% lactic acid was added to the mixture. The mixture was refluxed for 1 hour. The mixture was allowed to cool at room temperature, and then was allowed to cool to below 5° C. for 5 hours. The pale yellow solid was isolated by filtration. The pale yellow solid was 5.6 g after dried. The melting point of the pale yellow solid was 239-248° C.

Example 26

Preparation of the Medicaments

Preparation of coated tablets:
Formula of the core of the tablets:

| | |
|---|---|
| Compound 1 | 50 g |
| microcrystalline cellulose | 150 g |
| lactose | 50 g |
| Carboxy Methyl Starch Soluble | 25 g |
| Carboxy Methyl Cellulose | 15 g |
| silicon dioxide | 1.5 g |
| For | 1000 Tablets |

The process: the exact weight of compound I and lactose was mixed, then silicon dioxide was added to the mixture in order to increase the fluidity. Other pharmaceutical adjuvants were added and mixed, followed by tabletting.

Formula of the coating liquid: Oradry 25 g, in a suitable amount of 80% ethanol as coating.

Preparation of Injection:
Formula of the injection:

| | |
|---|---|
| Compound I | 50 g |
| Tween-80 | 20 g |
| Ethanol | 30 g |
| Water | added to 10,000 mL |
| For | 1000 vials |

The process: the exact weight of compound I and Tween-80 was mixed, 0.3% ethanol was added to the mixture to dissolve compound I and Tween-80 with heating. The liquid was filtered with 0.22 μm filter membrane under aseptic conditions, and then filled 10 ml per vial, and autoclaved.

Example 27

Compound I Inhibits Cancer Cell Growth In Vitro

The anti-cancer activities of COMPOUND I were evaluated using the microtetrazoline (MTT) and sulforhodamine B (SRB) assays. It is found that COMPOUND I significantly inhibited growth in vitro of many types of cancers, including breast cancer, lymphoma, leukemia, osteosarcoma, ovarian cancer, liver cancer, prostate cancer, pancreatic cancer, bladder cancer, prostate cancer, stomach cancer, lung cancer, colon cancer, nasopharyngeal carcinoma, and kidney cancer. The $IC_{50}$ of Compound I ranges between about 0.5 to about 3 μM for most cancer types. For example, the $IC_{50}$ of Compound I for H-22 liver cancer cells is 2.24 μg/ml, for Lewis lung carcinoma cells is 2.81 μg/ml, and for leukemia cells is 2.5 μg/ml.

Pulse-exposure studies, using methods as described in Kubota et al., Cancer Res. 1998; 58: 3370-3375 and Campbell et al., J. Mol. Endocrinol. 1997; 19:15-27, showed that compound I can markedly inhibit clonal growth of LNCap, PC-3 and Du145 prostate cancer cells, with a 50% inhibition ($ED_{50}$) of approximately 18 μg/ml. Specifically, a 5-day pulse-exposure to compound I (18 mg/ml) in liquid culture achieved a 50% inhibition of PC-3 clonal growth in soft agar, suggesting that the growth inhibition mediated by compound I remained after removal of compound I. Compound I is also shown to inhibit the clonal proliferation of a variety of malignant cells in vitro, including prostate and breast cancers, neuroepithelioma, melanoma, and Leukemia. It induces cell cycle arrest and apoptosis of some of these cells and inhibited the growth of LNCap and PC-3 types of cancer cells.

Example 28

Compound I Inhibits Cancer Cell Growth In Vivo

To determine if Compound I could inhibit primary tumor growth, syngeneic mice (C57B 16/J) bearing subcutaneous Lewis lung carcinomas and H-22 liver cancer were treated with Compound I with daily intralesional injections of (50 mg/kg) 1 mg of Compound I per 20 g mouse body weight. As shown in Table 1 below, primary tumor growth was inhibited during the 14 days treatment period.

Inhibition of primary tumor growth was first observed at dose of 20 mg/kg/day. Increased doses of Compound I correlated with increased efficacy of tumor inhibition. Inhibition of metastatic growth occurred at doses of approximately 20 mg/kg/day. There was no detectable toxicity. In contrast, tumor in animals treated with saline grew rapidly in size to >6.000 $mm^3$, leading to the demise of all animals on day 17 after tumor implantation.

TABLE 1

Inhibition of Lewis Lung Carcinoma Growth by COMPOUND I in Nude Mice

| | | Days | | | | | | | | |
|---|---|---|---|---|---|---|---|---|---|---|
| | | 2 | 4 | 6 | 8 | 10 | 12 | 14 | 16 | 17 |
| Tumor vol. ($mm^3$) | ZW 105 Treatment | 200 | 300 | 500 | 700 | 900 | 1200 | 1500 | 1800 | 2200 |
| | Control (Saline) | 200 | 500 | 1400 | 1800 | 2500 | 4000 | 5500 | 6200 | 6400 |

The in vivo anti-cancer activities of COMPOUND I were further evaluated using various other human cancer cells transplanted to nude mice. It is discovered that COMPOUND I inhibits in vivo growth of many types of human cancers.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. All references cited hereinabove and/or listed below are hereby expressly incorporated by reference.

I claim:

1. A compound having the following formula:

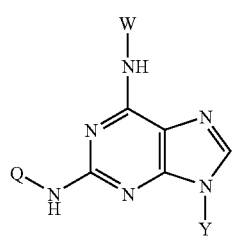

(A)

wherein
W represents a hydrogen, an optionally substituted $C_{1-6}$ alkyl, an optionally substituted $C_{3-6}$ cycloalkyl, or an optionally substituted $C_{1-6}$ haloalkyl,
Y represents a hydrogen, or a saccharide,
Q represents one selected from the group consisting of:

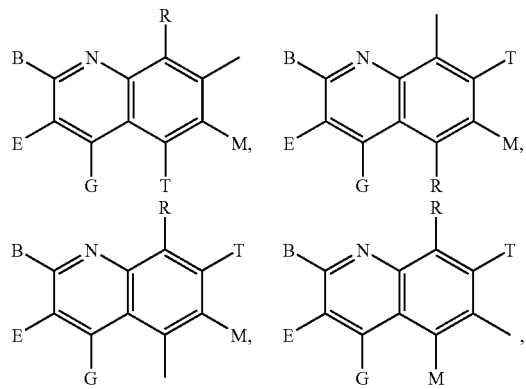

-continued

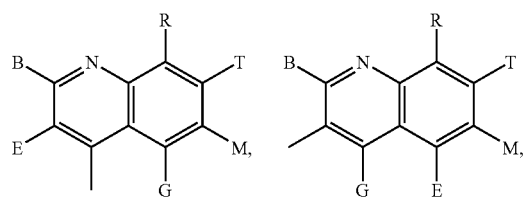

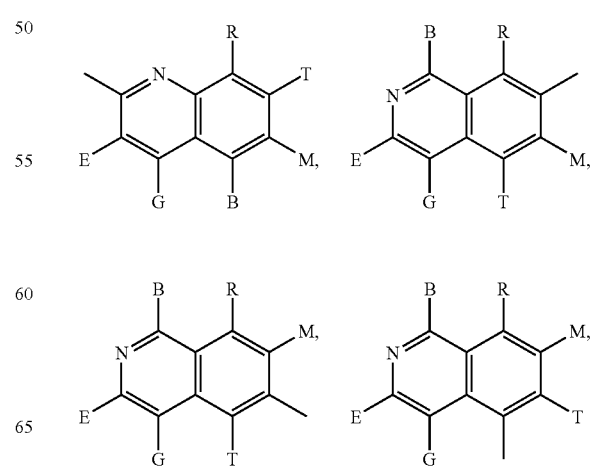

-continued

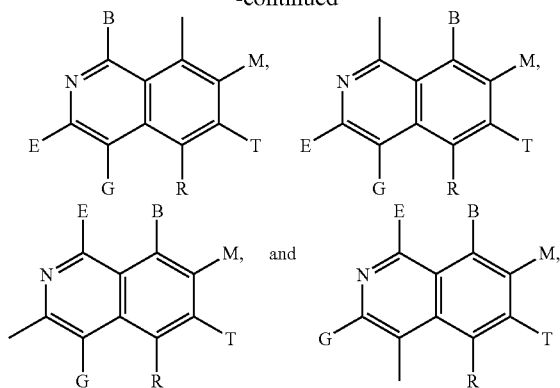

wherein B, E, G, R, T, and M each independently represents a hydrogen, an C1-6 alkyl, an C3-6 haloalkyl, a halogen, a cyano, or a amino, in the form of a racemate, a pure stereoisomer, or in the form of a mixtures of stereoisomers in any mixing ratio, in the illustrated form or in the form of an acid, a base or in the form of a salt or a solvate.

2. The compound according to claim 1, wherein the compound is in the form of a physiologically acceptable salt, or in the form of a hydrate.

3. The compound according to claim 1, wherein Y is a saccharide selected from the group consisting of:

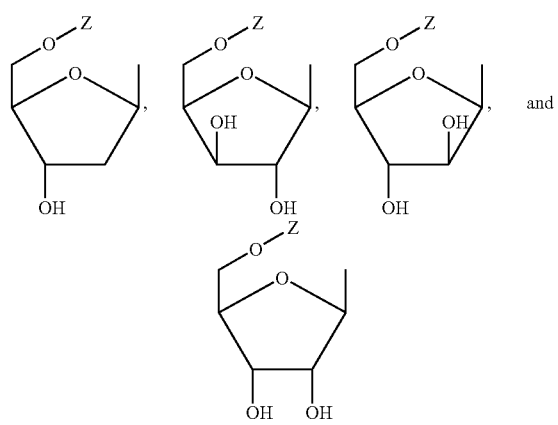

wherein Z represents a hydrogen, or one selected from the group consisting of:

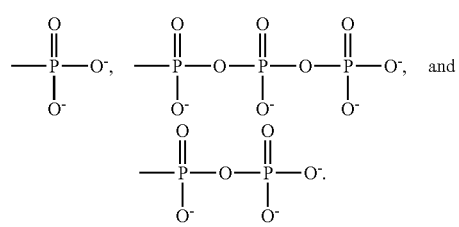

4. The compound according to claim 1, wherein W represents a hydrogen or one selected from the group consisting of:

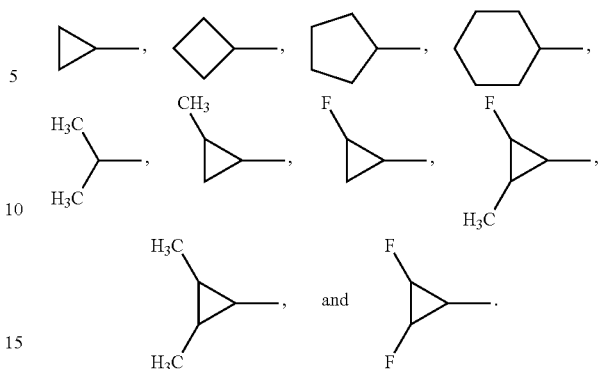

5. The compound according to claim 1, wherein Y represents a hydrogen.

6. The compound according to claim 1, wherein W is

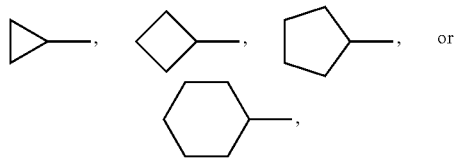

and wherein B, E, G, R, T, or M represents hydrogen.

7. The compound according to claim 1, wherein W is:

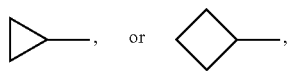

and wherein Q represents one of the a following:

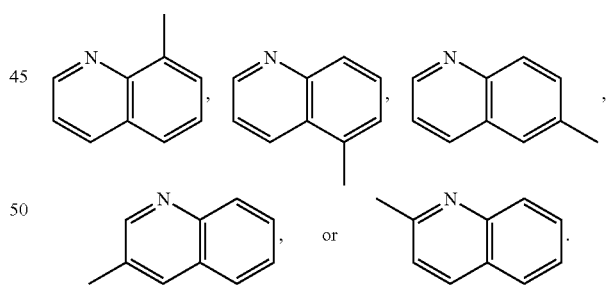

8. The compound according to claim 1, wherein Q represents

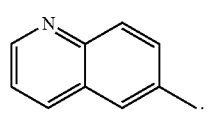

9. The compound according to claim 1, wherein According to claim 1 wherein the compound is one selected from the group consisting of:

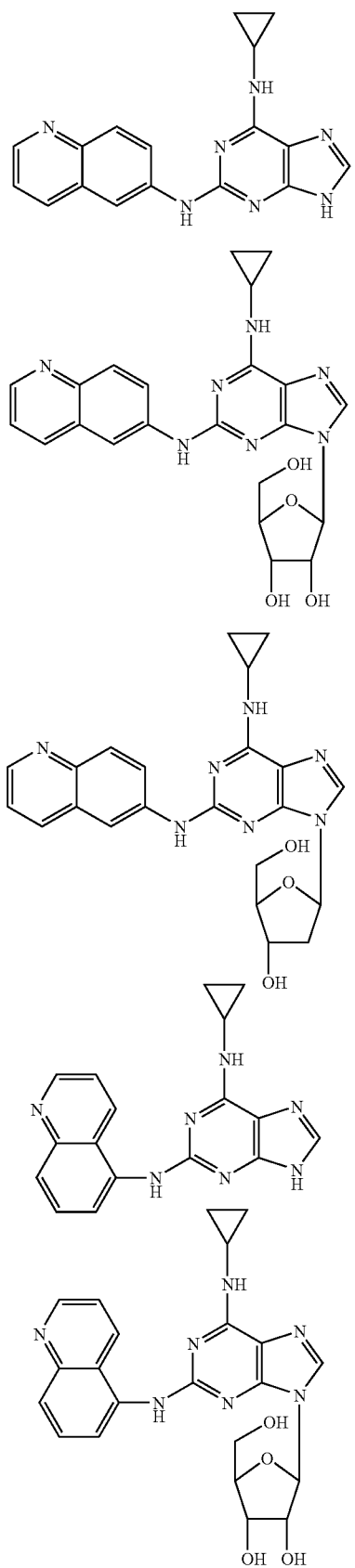

XI
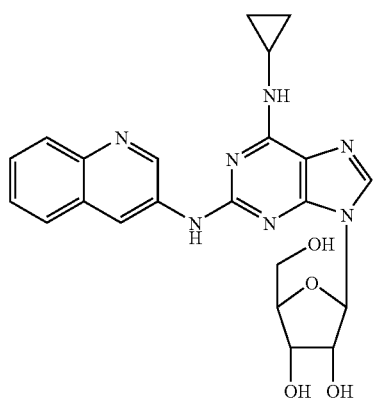
XII
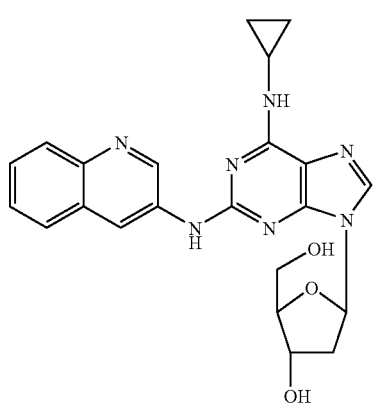
XIII
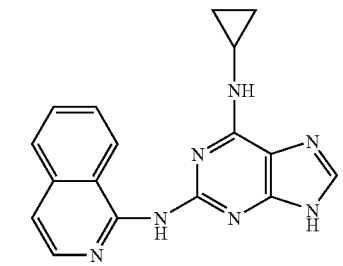
XIV
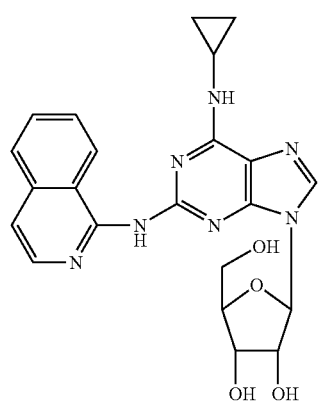
XV
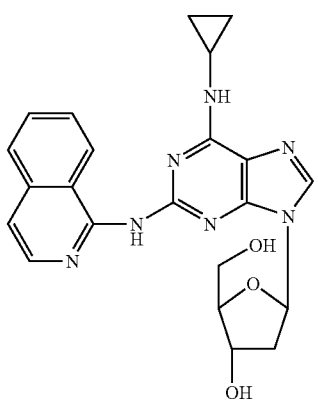
XVI
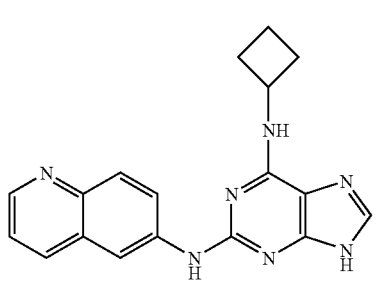
XVII
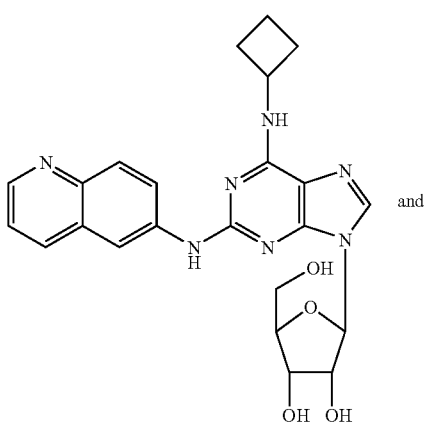
and
XVIII
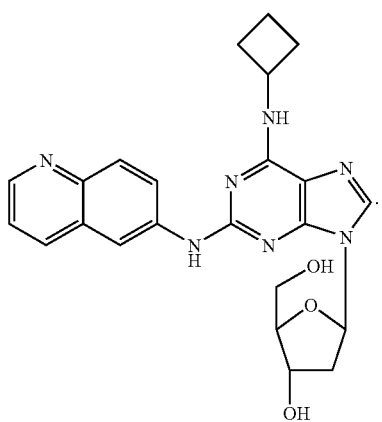

10. The compound according to claim 1, wherein the compound is:

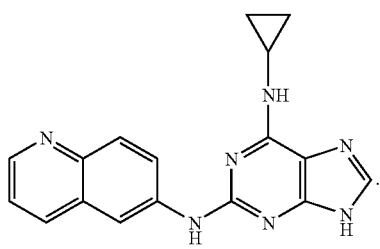

(I)

11. A physiologically acceptable salt of the compound according to claim 1, wherein the salt is formed between the compound and an inorganic acid, an organic acid or a base.

12. The physiologically acceptable salt according to claim 11, wherein the acid is hydrochloride, hydrobromide, hydroiodate, p-toluenesulfonate, phosphate, sulphate, perchloride, acetate, trifluoroacetate, propionate, citrate, malonate, succinate, lactate, oxalate, tartrate, or benzoate.

13. A pharmaceutical composition comprising a therapeutically effective amount of the compound of claim 1 and a pharmaceutically acceptable excipient.

14. A method for treating cancer, comprising administering to a patient in need thereof a therapeutically effective amount of the pharmaceutical composition of claim 13.

15. The method according to claim 14, wherein the cancer to be treated is selected from the group consisting of lung cancer, liver cancer, leucocythaemia, osteocarcinoma, pancreas cancer, skin cancer, melanoma, metrocarcinoma, oophoroma, rectal carcinoma, gastric carcinoma, colon cancer, breast carcinoma, salpinx carcinoma, endometrial carcinoma, cervix carcinoma, vagina carcinoma, carcinoma of vulva, esophagus carcinoma, small intestine carcinoma, incretion carcinoma, soft tissue sarcoma, urethra carcinoma, prostatic cancer, lymphocytoma, bladder cancer, nephridium cancer, tumors of vertebral column, tumors in the neuroglia of the brain, and pituitary adenoma.

16. The method according to claim 15, wherein the cancer is a liver cancer, Lewis lung carcinoma, or prostate cancer.

17. A method for producing a compound of claim 1, the method comprising (1) reacting compound (j)

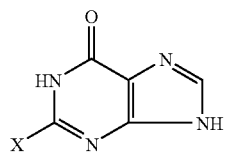

(j)

with Q—NH$_2$ in an organic solvent at a temperature of about 50 to about 150° C., to result in a first reaction mixture, followed by adding water to the first reaction mixture, and cooling the first reaction mixture at room temperature, to produce compound (b);

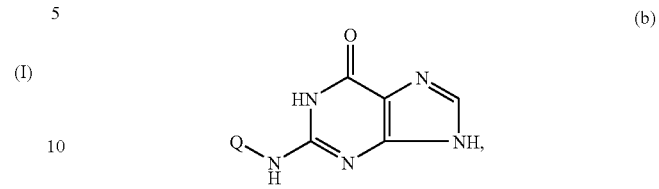

(b)

(2) reacting compound (b) with a halogenating agent in an organic solvent at about 50 to about 150° C. to result in a second reaction mixture, followed by adding water to the second reaction mixture and adjusting pH of the second reaction mixture to about pH 2-5 with acid, and allowing the second reaction mixture to cool at room temperature, to produce compound (c):

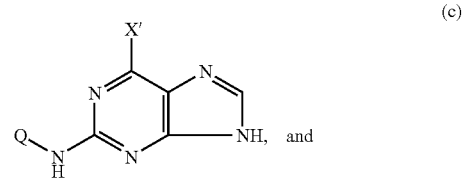

(c)

(3) reacting compound (c) in an organic solvent with W—NH$_2$ in the presence of an acid acceptor at a temperature of about 50-150° C., followed by distilling off the solvent, to result in compound (f)

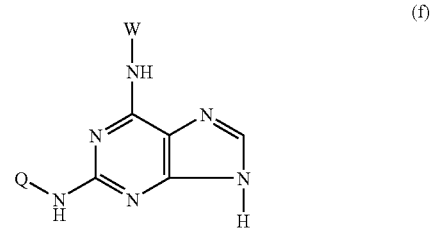

(f)

wherein X represents Br, X' represents Cl, and W and Q are as defined as claim 1.

18. The method according to claim 17, wherein each of steps (1), (2) or (3) is carried out for about 1-72 hours.

19. The method according to claim 17, wherein in Step (1) the molar ratio between compound (j) and Q—NH$_2$ is about 0.8 to 1.5.

20. The method according to claim 17, wherein in Step (3) the molar ratio between compound (b) and W—NH$_2$ is about 0.8 to 1.5.

21. A method for producing a compound of claim 1, the method comprising (1) reacting compound (k):

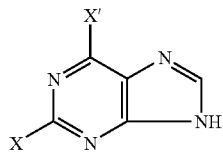

(k)

with W—NH$_2$ in an organic solvent and in the presence of an acid acceptor at a temperature of about 30-150° C., followed by distilling off the solvent, to produce compound (e):

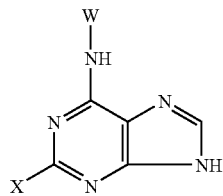

(e)

(2) reacting in an organic solvent compound (e) with Q—NH$_2$, in the presence of an acid acceptor at a temperature of about 70-170° C., followed by distilling off the solvent to produce compound (f):

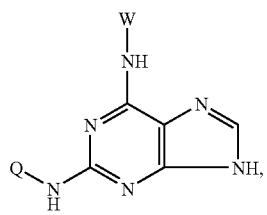

(f)

wherein X represents Cl, X' represents Cl, W and Q are as defined as claim 1.

22. The method according to claim 21, wherein each of steps (1) or (2) or (3) is carried out for about 1-72 hours.

23. The method according to claim 21, wherein in Step (1) the molar ratio between compound (k) and W—NH$_2$ is about 0.8 to 1.5.

24. The method according to claim 21, wherein in Step (2) the molar ratio between compound (b) and Q—NH$_2$ is about 0.8 to 1.5.

* * * * *